(12) United States Patent
Bhatnagar et al.

(10) Patent No.: US 6,395,919 B1
(45) Date of Patent: May 28, 2002

(54) CALCILYTIC COMPOUNDS

(75) Inventors: Pradip Kumar Bhatnagar, Exton; Joelle Lorraine Burgess, Phoenixville; James Francis Callahan, Philadelphia; Raul Rolando Calvo, Royersford, all of PA (US); Eric G. Del Mar, Salt Lake City, UT (US); Maria Amparo Lago, Audubon; Thomas The Nguyen, King of Prussia, both of PA (US)

(73) Assignees: SmithKline Beecham Corporation, Philadelphia, PA (US); NPS Pharmaceuticals, Salt Lake City, UT (US)

( * ) Notice: Subject to any disclaimer, the term of this patent is extended or adjusted under 35 U.S.C. 154(b) by 0 days.

(21) Appl. No.: 09/647,793

(22) PCT Filed: Apr. 8, 1999

(86) PCT No.: PCT/US99/07722

§ 371 (c)(1),
(2), (4) Date: Oct. 5, 2000

(87) PCT Pub. No.: WO99/51569

PCT Pub. Date: Oct. 14, 1999

Related U.S. Application Data

(60) Provisional application No. 60/081,093, filed on Apr. 8, 1998.

(51) Int. Cl.$^7$ .................. C07C 255/03; C07C 229/10
(52) U.S. Cl. .................. 558/414; 560/36; 562/451
(58) Field of Search .................. 558/414; 548/473; 562/451; 560/36

(56) References Cited

U.S. PATENT DOCUMENTS 4,645,678 A * 2/1987 Nofre et al. ................ 426/548
5,723,489 A   3/1998 Philip et al.

FOREIGN PATENT DOCUMENTS

| DE | WO 97 37967 | 10/1997 |
| EP | 0 764 632 A | 3/1997 |
| WO | 33 01 198 A | 7/1984 |

* cited by examiner

*Primary Examiner*—Floyd D. Higel
*Assistant Examiner*—Ebenezer Sackey
(74) *Attorney, Agent, or Firm*—Soma G. Simon; William T. King; Charles M. Kinzig

(57) ABSTRACT

Novel calcilytic compounds, pharmaceuticals compositions cotaining said compounds and their use as calcium receptor antagonists.

13 Claims, No Drawings

CALCILYTIC COMPOUNDS

This application is a 371 of PCT/US99/07722 filed Apr. 8, 1999 which claims benefit of provisional application No. 60/081,093 filed Apr. 8, 1998.

FIELD OF INVENTION

The present invention relates to novel calcilytic compounds, pharmaceutical compositions containing these compounds and their use as calcium receptor antagonists.

In mammals, extracellular $Ca^{2+}$ is under rigid homeostatic control and regulates various processes such as blood clotting, nerve and muscle excitability, and proper bone formation. Extracellular $Ca^{2+}$ inhibits the secretion of parathyroid hormone ("PTH") from parathyroid cells, inhibits bone resorption by osteoclasts, and stimulates secretion of calcitonin from C-cells. Calcium receptor proteins enable certain specialized cells to respond to changes in extracellular $Ca^{2+}$ concentration.

PTH is the principal endocrine factor regulating $Ca^{2+}$ homeostasis in the blood and extracellular fluids. PTH, by acting on bone and kidney cells, increases the level of $Ca^{2+}$ in the blood. This increase in extracellular $Ca^{2+}$ then acts as a negative feedback signal, depressing PTH secretion. The reciprocal relationship between extracellular $Ca^{2+}$ and PTH secretion forms an important mechanism maintaining bodily $Ca^{2+}$ homeostasis.

Extracellular $Ca^{2+}$ acts directly on parathyroid cells to regulate PTH H secretion. The existence of a parathyroid cell surface protein which detects changes in extracellular $Ca^{2+}$ has been confirmed. See Brown et al., Nature 366:574, 1993. In parathyroid cells, this protein, the calcium receptor, acts as a receptor for extracellular $Ca^{2+}$, detects changes in the ion concentration of extracellular $Ca^{2+}$, and initiates a functional cellular response, PTH secretion.

Extracellular $Ca^{2+}$ influences various cell functions, reviewed in Nemeth et al., Cell Calcium 11:319, 1990. For example, extracellular $Ca^{2+}$ plays a role in parafollicular (C-cells) and parathyroid cells. See Nemeth, Cell Calcium 11:323, 1990. The role of extracellular $Ca^{2+}$ on bone osteoclasts has also been studied. See Zaidi, Bioscience Reports 10:493, 1990.

Various compounds are known to mimic the effects of extra-cellular $Ca^{2+}$ on a calcium receptor molecule. Calcilytics are compounds able to inhibit calcium receptor activity, thereby causing a decrease in one or more calcium receptor activities evoked by extracellular $Ca^{2+}$. Calcilytics are useful as lead molecules in the discovery, development, design, modification and/or construction of useful calcium modulators which are active at $Ca^{2+}$ receptors. Such calcilytics are useful in the treatment of various disease states characterized by abnormal levels of one or more components, e.g., polypeptides such as hormones, enzymes or growth factors, the expression and/or secretion of which is regulated or affected by activity at one or more $Ca^{2+}$ receptors. Target diseases or disorders for calcilytic compounds include diseases involving abnormal bone and mineral homeostasis.

Abnormal calcium homeostasis is characterized by one or more of the following activities: an abnormal increase or decrease in serum calcium; an abnormal increase or decrease in urinary excretion of calcium; an abnormal increase or decrease in bone calcium levels (for example, as assessed by bone mineral density measurements); an abnormal absorption of dietary calcium; an abnormal increase or decrease in the production and/or release of messengers which affect serum calcium levels such as PTH and calcitonin; and an abnormal change in the response elicited by messengers which affect serum calcium levels.

Thus, calcium receptor antagonists offer a unique approach towards the pharmacotherapy of diseases associated with abnormal bone or mineral homeostasis, such as hypoparathyroidism, osteosarcoma, periodontal disease, fracture healing, osteoarthritis, rheumatoid arthritis, Paget's disease, humoral hypercalcemia associated with malignancy and fracture healing, and osteoporosis.

SUMMARY OF THE INVENTION

The present invention comprises novel calcium receptor antagonists represented by Formula (I) hereinbelow and their use as calcium receptor antagonists in the treatment of a variety of diseases associated with abnormal bone or mineral homeostasis, including but not limited to hypoparathyroidism, osteosarcoma, periodontal disease, fracture healing, osteoarthritis, rheumatoid arthritis, Paget's disease, humoral hypercalcemia associated with malignancy and fracture healing, and osteoporosis.

The present invention further provides a method for antagonizing calcium receptors in an animal, including humans, which comprises administering to an animal in need thereof an effective amount of a compound of Formula (I), indicated hereinbelow.

The present invention further provides a method for increasing serum parathyroid levels in an animal, including humans, which comprises administering to an animal in need thereof an effective amount of a compound of Formula (I), indicated hereinbelow.

DETAILED DESCRIPTION OF THE INVENTION

The compounds of the present invention are selected from Formula (I) hereinbelow:

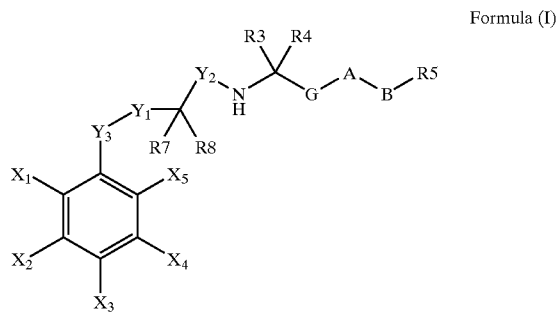

Formula (I)

wherein:

$Y_1$ is a covalent bond, alkylene or alkenylene of up to 4 carbon atoms, unsubstituted or substituted by $C_{1-4}$ alkyl, or O;

$Y_2$ is methylene, unsubstituted or substituted by $C_{1-4}$ alkyl or haloalkyl;

$Y_3$ is covalent bond or O, S, N—$R^{IV}$ or $C_{1-4}$ alkylene-O, $C_{1-4}$ alkylene-S, $C_{1-4}$ alkylene-N—$R^{IV}$;

$R_3$ and $R_4$ are, independently, methyl or ethyl, or, together, form cyclopropyl;

$R_5$ is aryl or fused aryl, dihydro or tetrahydro fused aryl, unsubstituted or substituted with any substituents being selected from the group consisting of OH, halogen, $C_{1-4}$ alkyl, $C_{1-4}$ alkoxy, $C_{3-6}$ cycloalkyl, $OSO_2R^{IV}$, CN, $NO_2$, $OCF_3$, $CF_3$, $CH_2CF_3$, $(CH_2)_n$ $CO_2R^{IV}$, and O—(CH$_2$)$_n$ CO$_2$R$^{IV}$, wherein n is an integer from 0 to 3 and R$^{IV}$ is selected from the group consisting of H, C$_{1-4}$ alkyl, C$_{3-6}$ cycloalkyl;

or R$_5$ is heteroaryl or fused heteroaryl; wherein the hetero-ring contains N, O or S, and is aromatic, dihydro or tetrahydro, unsubstituted or substituted with any substituents being selected from the group consisting of OH, OCH$_3$, CH(CH$_3$)$_2$, halogen, C$_{1-4}$ alkyl, C$_{1-4}$ alkoxy, C$_{3-6}$ cycloalkyl, OSO$_2$R$^{IV}$, CN, NO$_2$, OCF$_3$, CF$_3$, CH$_2$CF$_3$, (CH$_2$)$_n$ CO$_2$H, (CH$_2$)$_n$ CO$_2$R$^{IV}$, and O—(CH$_2$)$_n$ CO$_2$R$^{IV}$;

G is a covalent bond, CHR$_6$ or C—R$_6$ wherein R$_6$ is H, OH or O (forming a ketone);

R$_7$ is H, OH, or O—C$_{1-4}$ alkyl;

R$_8$ is H or C$_{1-4}$ alkyl; or R$_7$ and R$_8$ together form a ketone;

A and B are, independently, selected from the group consisting of a bond, CH$_2$, NH, O, S and C=O, provided that either A or B is selected from CH$_2$ and NH; or A and B together form a bond; or the A-B moiety is represented by CH=CH or C≡C; wherein X$_1$ and X$_5$ are independently selected from the group consisting of H, halogen, CN, NO$_2$, C$_{1-4}$ alkyl, cycloalkyl, CH$_2$-aryl, and CH$_2$-heteroaryl; provided that either X$_1$ or X$_5$ is H; X$_2$, X$_3$ and X$_4$ are selected from the group consisting of H, halogen, O—C$_{1-4}$ alkyl, O-aryl, O-heteroaryl, CH$_2$-aryl. CH$_2$-heteroaryl, alkyl, C(O)aryl, C(O)heteroaryl, CH(OH)aryl, CH(OH)heteroaryl; and J—K;

J is a covalent bond, alkylene, O-alkylene or alkenylene of up to 5 carbon atoms, unsubstituted or substituted by a substituent selected from the group consisting of C$_{1-4}$ alkyl, OH, O(forming a ketone), aryl, heteroaryl, and NR'R", wherein R' and R" are independently selected from the group consisting of H, alkyl, aryl, heteroaryl, C(O)alkyl, C(O)aryl, and C(O)heteroaryl;

K is selected from the group consisting of, CO$_2$R$^{IV}$, OH, and CN;

and pharmaceutically acceptable salts and complexes thereof.

Preferably, the compounds of the present invention have a structure according to Formula (II):

Formula (II)

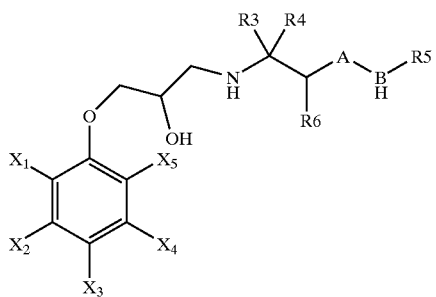

wherein:

R$_3$ and R$_4$ are, independently, methyl or ethyl, or, together, form cyclopropyl;

R$_5$ is aryl or fused aryl, or dihydro or tetrahydro fused aryl, unsubstituted or substituted with any substituents being selected from the group consisting of OH, halogen, C$_{1-4}$ alkyl, C$_{1-4}$ alkoxy, C$_{3-6}$ cycloalkyl, OSO$_2$R$^{IV}$, CN, NO$_2$, OCF$_3$, CF$_3$, CH$_2$CF$_3$, wherein R$^{IV}$ is selected from the group consisting of H, C$_{1-4}$ alkyl, C$_{3-6}$ cycloalkyl, C$_{3-6}$ cycloalkyl;

or R$_5$ is heteroaryl or fused heteroaryl; wherein the hetero-ring contains N, O or S and is aromatic, dihydro or tetrahydro, unsubstituted or substituted with any substituents being selected from the group consisting of OH, OCH$_3$, CH(CH$_3$)$_2$, halogen, C$_{1-4}$ alkyl, C$_{1-4}$ alkoxy, C$_{3-6}$ cycloalkyl, CN, NO$_2$, OCF$_3$, CF$_3$, CH$_2$CF$_3$;

R$_6$ is H, OH or O (forming a ketone); and

A and B are, independently, selected from the group consisting of a bond, CH$_2$, NH, O, S and C=O, provided that either A or B is selected from CH$_2$ and NH; or A and B together form a bond; or the A-B moiety is represented by CH=CH or C≡C.

X$_1$ and X$_5$ are independently selected from the group consisting of H, halogen, CN, NO$_2$, C$_{1-4}$ alkyl, cycloalkyl, CH$_2$-aryl, and CH$_2$-heteroaryl; provided that either X$_1$ or X$_5$ is H; X$_2$, X$_3$ and X$_4$ are selected from the group consisting of H, halogen, O—C$_{1-4}$ alkyl, O-aryl. O-heteroaryl, CH$_2$-aryl, CH$_2$-heteroaryl, alkyl, C(O)aryl, C(O)heteroaryl, CH(OH)aryl, and CH(OH)heteroaryl and J—K J is a covalent bond, alkylene, O-alkylene or alkenylene of up to 5 carbon atoms, unsubstituted or substituted by a substituent selected from the group consisting of C$_{1-4}$ alkyl, OH, O(ketone), aryl, heteroaryl, and NR'R", wherein R' and R" are independently selected from the group consisting of H, alkyl, aryl, heteroaryl, C(O)alkyl, C(O)aryl, and C(O) heteroaryl;

K is selected from the group consisting of CO$_2$H, CO$_2$R$^{IV}$, OH, and CN.

More preferably, R$_5$ is aryl or fused aryl or dihydro or tetrahydro aryl, unsubstituted or substituted with any substituents being selected from the group consisting of OCH$_3$, CH$_2$CH$_3$, halogen, C$_{3-6}$ heterocycloalkyl, CN, NO$_2$, OCF$_3$, CF$_3$, CH$_2$CF$_3$; or R$_5$ is heteroaryl or fused heteroaryl, wherein the hetero-ring contains N, O or S and is aromatic, dihydro or tetrahydro, unsubstituted or substituted with any substituents being selected from the group consisting of OCH$_3$, halogen, C$_{1-4}$ alkyl, CN, NO$_2$, OCF$_3$, CF$_3$, CH$_2$CF$_3$;

R$_6$ is H; and

A and B are, independently, selected from the group consisting of a bond, CH$_2$, NH, O, S and C=O, provided that either A or B is selected from CH$_2$ and NH, or A and B together form a bond.

X$_1$ and X$_5$ are selected from the group consisting of Cl, F, CN, and NO$_2$; provided that either X$_1$ or X$_5$ is H;

X$_2$, X$_3$ and X$_4$ is selected from the group consisting of H,F, Cl, CN, O-aryl, O-heteroaryl, CH$_2$-aryl, CH$_2$-heteroaryl, C(O)aryl, C(O)heteroaryl, CH(OH)aryl, CH(OH)heteroaryl or J—K J is a covalent bond, alkylene, alkenylene or O alkylene of up to 5 carbon atoms, unsubstituted or substituted by C$_{1-4}$ alkyl, aryl, heteroaryl, or NR'R", wherein R' and R" are independently selected from the group consisting of H, alkyl, aryl, heteroaryl, C(O)alkyl, C(O)aryl, and C(O)heteroaryl;

K is CO$_2$R$^{IV}$;

Most preferably, R$_5$ is phenyl, naphthyl, heteroaryl or fused heteroaryl, wherein the heteroring contains N, O or S, and is aromatic, dihydro or tetrahydro; unsubstituted or substituted with any substituents being selected from the group consisting of halogen, OCH$_3$, CF$_3$, and C$_{1-4}$alkyl;

R$_6$ is H; and

A and B are, independently, selected from the group consisting of a bond, CH$_2$, O, or A and B together form a bond.

$X_1$ and $X_5$ are independently Cl, CN, or $NO_2$; provided that either $X_1$ or $X_5$ is H;

$X_2$ or $X_3$ or $X_4$ are H, CN, Cl or J—K;

J is a covalent bond, alkylene or alkenylene of up to 5 carbon atoms, unsubstituted or substituted by aryl, heteroaryl, or NR'R", wherein R' and R" are selected from the group consisting of H, alkyl, aryl, heteroaryl, C(O)alkyl, C(O)aryl, and C(O) heteroaryl;

K is $CO_2R^{IV}$.

Preferred heteroaryls useful in the present invention include unsubstituted and substituted quinolines, isoquinolines, benzofurans, dihydrobenzofurans, benzothiophenes, dihydrobenzothiophenes and pyridines.

As used herein "cycloalkyl" refers to optionally substituted 3–7 membered carbocyclic rings wherein any substituents are selected from the group consisting of, F, Cl, Br, I, $N(R^{IV})_2$, $SR^{IV}$ and O $R^{IV}$ unless otherwise indicated.

As used herein "heterocycloalkyl" refers to optionally substituted 4, 5, 6 or 7 membered heterocyclic rings containing 1 to 2 heteroatoms selected from N, O, and S.

As used herein, "aryl" refers to an optionally substituted aromatic group with at least one ring having a conjugated pi-electron system, containing up to two conjugated or fused ring systems. Aryl includes carbocyclic aryl, and biaryl groups, all of which may be optionally substituted. Preferred aryl include phenyl and naphthyl. More preferred aryl include phenyl. Preferred substituents are selected from the group consisting of halogen, $C_{1-4}$ alkyl, $OCF_3$, $CF_3$, OMe, CN, $OSO_2$ R and $NO_2$, wherein R represents $C_{1-4}$ alkyl or $C_{3-6}$ cycloalkyl.

As used herein, "acyl" refers to $C_{1-4}$ alkylcarbonyl.

As used herein, "alkenyl" refers to an optionally substituted hydrocarbon group containing at least one carbon-carbon double bond and containing up to 5 carbon atoms joined together. The alkenyl hydrocarbon chain may be straight, branched or cyclic. Any substituents are selected from the group consisting of halogen, $C_{1-4}$ alkyl, $OCF_3$, $CF_3$, OMe, CN, $OSO_2$ R and $NO_2$, wherein R represents $C_{1-4}$ alkyl or $C_{3-6}$ cycloalkyl.

As used herein, "alkynyl" refers to an optionally substituted hydrocarbon group containing at least one carbon-carbon triple bond between the carbon atoms and containing up to 5 carbon atoms joined together. The alkynyl hydrocarbon group may be straight-chained, branched or cyclic. Any substituents are selected from the group consisting of halogen, $C_{1-4}$ alkyl, $OCF_3$, $CF_3$, OMe, CN, $OSO_2$ R and $NO_2$, wherein R represents $C_{1-4}$ alkyl or $C_{3-6}$ cycloalkyl.

The compounds of the present invention may contain one or more asymmetric carbon atoms and may exist in racemic and optically active forms. All of these compounds and diastereomers are contemplated to be within the scope of the present invention.

Preferred compounds of the present inventions include:

(R)-N-[2-Hydroxy-3-(2-cyano-4-(2-carboethoxyethyl) phenoxy)propyl]-1,1-dimethyl-2-(2-naphthyl) ethylamine;

(R)-N-[2-Hydroxy-3-(2-cyano-4-(2-carboxyethyl) phenoxy)propyl]-1,1-dimethyl-2-(2-naphthyl) ethylamine;

(R)-N-[2-Hydroxy-3-(2-cyano-5-(3-carbethoxypropyl) phenoxy)propyl]-1,1-dimethyl-2-(2-naphthyl) ethylamine;

(R)-N-[2-Hydroxy-3-(2-cyano-5-(3-carboxypropyl) phenoxy)propyl]-1,1-dimethyl-2-(2-naphthyl) ethylamine;

(R)-N-[2-Hydroxy-3-(2-cyano-5-(2-carbethoxyethyl) phenoxy)propyl]-1,1-dimethyl-2-(2-naphthyl) ethylamine;

(R)-N-[2-Hydroxy-3-(2-cyano-5-(2-carboxyethyl) phenoxy)propyl]-1,1-dimethyl-2-(2-naphthyl) ethylamine;

(R)-N-[2-Hydroxy-3-(2-cyano-4-(3-carbethoxypropyl) phenoxy)propyl]-1,1-dimethyl-2-(2-naphthyl) ethylamine;

(R)-N-[2-Hydroxy-3-(2-cyano-4-(3-carboxypropyl) phenoxy)propyl]-1,1-dimethyl-2-(2-naphthyl) ethylamine;

(R)-N-[2-Hydroxy-3-(2-cyano-3-(3-carbethoxypropyl) phenoxy)propyl]-1,1-dimethyl-2-(2-naphthyl) ethylamine;

(R)-N-[2-Hydroxy-3-(2-cyano-3-(3-carboxypropyl) phenoxy)propyl]-1,1-dimethyl-2-(2-naphthyl) ethylamine;

(R)-N-[2-Hydroxy-3-(2-cyano-3-(2-carbethoxyethyl) phenoxy)propyl]-1,1-dimethyl-2-(2-naphthyl) ethylamine;

(R)-N-[2-Hydroxy-3-(2-cyano-3-(2-carboxyethyl) phenoxy)propyl]-1,1-dimethyl-2-(2-naphthyl) ethylamine;

(R)-N-[2-Hydroxy-3-(2-cyano-4-(carbethoxymethyl) phenoxy)propyl]-1,1-dimethyl-2-(2-naphthyl) ethylamine;

(R)-N-[2-Hydroxy-3-(2-cyano-4-(carboxymethyl) phenoxy)propyl]-1,1-dimethyl-2-(2-naphthyl) ethylamine;

(R)-N-[2-Hydroxy-3-(2-cyano-5-(carbethoxymethyl) phenoxy)propyl]-1,1-dimethyl-2-(2-naphthyl) ethylamine;

(R)-N-[2-Hydroxy-3-(2-cyano-5-(carboxymethyl) phenoxy)propyl]-1,1-dimethyl-2-(2-naphthyl) ethylamine;

(R)-N-[2-Hydroxy-3-(2-cyano-4-(2-carbethoxy-trans-ethylene)phenoxy)propyl]-1,1-dimethyl-2-(2-naphthyl)ethylamine;

(R)-N-[2-Hydroxy-3-(2-cyano-4-(2-carboxy-trans-ethylene)phenoxy)propyl]-1,1-dimethyl-2-(2-naphthyl)ethylamine;

(R)-1-[1,1-dimethyl-2-(4-methoxyphenyl)ethylamino]-3 (4-(2-phenyl-2-R,S-methoxycarbonylethyl))phenoxy]-propan-2-ol;

(R)-1-[1,1-dimethyl-2-(4-methoxyphenyl)ethylamino]-3-[(4-(2-phenyl-2-R,S-carboxyethyl))phenoxy]-propan-2-ol;

(R)-1-[1,1-dimethyl-2-(4-methoxyphenyl)ethylamino]-3-[(3-benzyl-4-methoxycarbonylmethyl)phenoxy]-propan-2-ol;

(R)-1-[1,1-dimethyl-2-(2-naphthyl)ethylamino]-3-[(3-benzyl-4-methoxycarbonylmethyl)phenoxy]-propan-2-ol;

(R)-1-[1,1-dimethyl-2-(2-naphthyl)ethylamino]-3-[(3-benzyl-4-carboxymethyl)phenoxy]-propan-2-ol;

(R)-1-[1,1-dimethyl-2-(4-methoxyphenyl)ethylamino]-3-[(3-benzyl-4-carboxymethyl)phenoxy]-propan-2-ol, (R)-1-[1,1-dimethyl-2-(4-methoxyphenyl)ethylamino]-3-[(4-(3-hydroxy)propyl)phenoxy]-propan-2-ol; (R)-1-[1,1-dimethyl-2-(4-methoxyphenyl)ethylamino]-3-[(4-(2-hydroxy)ethyl)phenoxy]-propan-2-ol; (R)-1-[1,1-dimethyl-2-(4-methoxyphenyl)ethylamino]-3-[(4-(2-cyano)ethyl)phenoxy]-propan-2-ol;

(R)-Methyl 2-[4-[3-[2-(4-methoxyphenyl)-1,1-dimethylethyiamino]-2-hydroxypropoxy]benzoylbenzoate;

(R)-2-[4-[3-[2-(4-Methoxyphenyl)-1,1-dimethylethylamino]-2-hydroxypropoxy]benzoylbenzoic acid;

(R)-1-[1,1-dimethyl-2-(4-methoxyphenyl)ethylamino]-3-[(4-cyanomethyl)phenoxy]-propan-2-ol;

(R)-1-[1,1-dimethyl-2-(4-methoxyphenyl)ethylamino]-3-[(4-cyano)phenoxy]-propan-2-ol;

(R)-1-[1,1-dimethyl-2-(4-methoxyphenyl)ethylamino]-3-[(4-methoxycarbonylmethyl)phenoxy]-propan-2-ol;

(R)-1-[1,1-dimethyl-2-(4-methoxyphenylethylamino]-3-[(2-nitro-4-cyano)phenoxy]-propan-2-ol;

(R)-1-[1,1-dimethyl-2-(4-methoxyphenyl)ethylamino]-3-[(2-nitro-4-(hydroxymethyl))phenoxy ]-propan-2-ol;

(R)-1-[1,1-dimethyl-2-(4-methoxyphenyl)ethylamino]-3-[(2-nitro-4-methoxycarbonylmethyl)phenoxy]-propan-2-ol;

(R)-1-[1,1-dimethyl-2-(4-methoxyphenyl)ethylamino]-3-[(2-nitro-4-carboxymethyl)phenoxy]-propan-2-ol;

(R)-1-[1,1-dimethyl-2-(2-naphthyl)ethylamino]-3-[(4-methoxycarbonyl)phenoxy]-propan-2-ol;

(R)-1-[1,1-dimethyl-2-(2-naphthyl)ethylamino]-3-[(4-carboxy)phenoxy]-propan-2-ol;

(R)-1-[1,1-dimethyl-2-(4-methoxyphenyl)ethylamino]-3-[(2-cyano-4-ethoxycarbonylmethyl)phenoxy]-propan-2-ol;

(R)-1-[1,1-dimethyl-2-(4-methoxyphenyl)ethylamino]-3-[(2-cyano-4-carboxymethyl)phenoxy]-propan-2-ol;

(R)-1-[1,1-dimethyl-2-(4-methoxyphenyl)ethylamino]-3-[(4-methoxycarbonylethyl)phenoxy]-propan-2-ol;

N-[2R-hydroxy-3-[[2-nitro-4-[2S-ethoxycarbonyl-2-[methylsulfonyl]amino]phenoxy]propyl]-1,1-dimethyl-2-[4-methoxyphenyl]ethylamine;

N-[2R-hydroxy-3-[[2-nitro-4-[2S-methoxycarbonyl-2-[phthalimido]phenoxy]propyl]-1,1-dimethyl-2-[naphthyl]ethylamine;

N-[2R-hydroxy-3-[[2-nitro-4-[2S-carboxy-2-[[[2-carboxy]phenyl]carbonyl]amino]ethyl]phenoxy]propyl]-1,1-dimethyl-2-[naphthyl]ethylamine;

N-[2R-hydroxy-3-[[2-nitro-4-[2S-methoxycarbonyl-2-[[[2-carboxy]phenyl]carbonyl]amino]ethyl]phenoxy]propyl]-1,1-dimethyl-2-[naphthyl]ethylamine;

(R)-1-[1,1-dimethyl-2-(2-naphthyl)ethylamino]-3-[(3-(2-aminophenoxy)-4-methoxycarbonyl)phenoxy]-propan-2-ol;

(R)-1-[1,1-dimethyl-2-(2-naphthyl)ethylamino]-3-[(3-(2-aminophenoxy)-4-carboxy)phenoxy]-propan-2-ol;

and pharmaceutically acceptable salts and complexes thereof.

More preferred compounds of the present invention include:

(R)-N-[2-Hydroxy-3-(2-cyano-4-(2-carboethoxyethyl)phenoxy)propyl]-1,1-dimethyl-2-(2-naphthyl)ethylamine;

(R)-N-[2-Hydroxy-3-(2-cyano-4-(2-carboxyethyl)phenoxy)propyl]-1,1-dimethyl-2-(2-naphthyl)ethylamine;

(R)-N-[2-Hydroxy-3-(2-cyano-5-(3-carbethoxypropyl)phenoxy)propyl]-1,1-dimethyl-2-(2-naphthyl)ethylamine;

(R)-N-[2-Hydroxy-3-(2-cyano-5-(3-carboxypropyl)phenoxy)propyl]-1,1-dimethyl-2-(2-naphthyl)ethylamine;

(R)-N-[2-Hydroxy-3-(2-cyano-5-(2-carbethoxyethyl)phenoxy)propyl]-1,1-dimethyl-2-(2-naphthyl)ethylamine; (R)-N-[2-Hydroxy-3-(2-cyano-5-(2-carboxyethyl)phenoxy)propyl]-1,1-dimethyl-2-(2-naphthyl)ethylamine;

(R)-N-[2-Hydroxy-3-(2-cyano-4-(3-carbethoxypropyl)phenoxy)propyl]-1,1-dimethyl-2-(2-naphthyl)ethylamine;

(R)-N-[2-Hydroxy-3-(2-cyano-4-(3-carboxypropyl)phenoxy)propyl]-1,1-dimethyl-2-(2-naphthyl)ethylamine;

(R)-N-[2-Hydroxy-3-(2-cyano-3-(3-carbethoxypropyl)phenoxy)propyl]-1,1-dimethyl-2-(2-naphthyl)ethylamine;

(R)-N-[2-Hydroxy-3-(2-cyano-3-(3-carboxypropyl)phenoxy)propyl]-1,1-dimethyl-2-(2-naphthyl)ethylamine;

(R)-N-[2-Hydroxy-3-(2-cyano-3-(2-carbethoxyethyl)phenoxy)propyl]-1,1-dimethyl-2-(2-naphthyl)ethylamine;

(R)-N-[2-Hydroxy-3-(2-cyano-3-(2-carboxyethyl)phenoxy)propyl]-1,1-dimethyl-2-(2-naphthyl)ethylamine;

(R)-N-[2-Hydroxy-3-(2-cyano-4-(carbethoxymethyl)phenoxy)propyl]-1,1-dimethyl-2-(2-naphthyl)ethylamine;

(R)-N-[2-Hydroxy-3-(2-cyano-4-(carboxymethyl)phenoxy)propyl]-1,1-dimethyl-2-(2-naphthyl)ethylamine;

(R)-N-[2-Hydroxy-3-(2-cyano-5-(carbethoxymethyl)phenoxy)propyl]-1,1-dimethyl-2-(2-naphthyl)ethylamine;

(R)-N-[2-Hydroxy-3-(2-cyano-5-(carboxymethyl)phenoxy)propyl]-1,1-dimethyl-2-(2-naphthyl)ethylamine;

(R)-N-[2-Hydroxy-3-(2-cyano-4-(2-carbethoxy-trans-ethylene)phenoxy)propyl]-1,1-dimethyl-2-(2-naphthyl)ethylamine;

(R)-N-[2-Hydroxy-3-(2-cyano-4-(2-carboxy-trans-ethylene)phenoxy)propyl]-1,1-dimethyl-2-(2-naphthyl)ethylamine;

(R)-1-[1,1-dimethyl-2-(2-naphthyl)ethylamino]-3-[(3-(2-aminophenoxy)4-methoxycarbonyl)phenoxy]-propan-2-ol;

(R)-1-[1,1-dimethyl-2-(4-methoxyphenyl)ethylamino]-3 (4-(2-phenyl-2-R,S-methoxycarbonylethyl))phenoxy]-propan-2-ol, (R)-1-[1,1-dimethyl-2-(4-methoxyphenyl)ethylamino]-3-[(3-benzyl-4-methoxycarbonylmethyl)phenoxy]-propan-2-ol;

(R)-1-[1,1-dimethyl-2-(2-naphthyl)ethylamino]-3-[(3-benzyl-4-methoxycarbonylmethyl)phenoxy]-propan-2-ol;

(R)-1-[1,1-dimethyl-2-(2-naphthyl)ethylamino]-3-[(3-benzyl-4-carboxymethyl)phenoxy]-propan-2-ol;

(R)-Methyl 2-[4-[3-[2-(4-methoxyphenyl)-1,1-dimethylethylamino]-2-hydroxypropoxy]benzoylbenzoate;

(R)-1-[1,1-dimethyl-2-(4-methoxyphenyl)ethylamino]-3-[(2-cyano-4-ethoxycarbonylmethyl)phenoxy]-propan-2-ol;

(R)-1-[1,1-dimethyl-2-(4-methoxyphenyl)ethylamino]-3-[(2-nitro-4-methoxycarbonylmethyl)phenoxy]-propan-2-ol;

(R)-1-[1,1-dimethyl-2-(2-naphthyl)ethylamino]-3-[(4-methoxycarbonyl)phenoxy ]-propan-2-ol; N-[2R-hydroxy-3-[[2-nitro-4-[2S-ethoxycarbonyl-2-[methylsulfonyl]amino]phenoxy]propyl]-1,1-dimethyl-2-[4-methoxyphenyl]ethylamine; N-[2R-hydroxy-3-[[2-nitro-4-[2S-methoxycarbonyl-2-[phthalimido]phenoxy]propyl]-1,1-dimethyl-2-[naphthyl]ethylamine;

N-[2R-hydroxy-3-[[2-nitro-4-[2S-methoxycarbonyl-2-[[[2-carboxy]phenyl]carbonyl]amino]ethyl]phenoxy] propyl]-1,1-dimethyl-2-[naphthyl]ethylamine; and
pharmaceutically acceptable salts and complexes thereof.

The most preferred compounds useful in the present invention include:

(R)-N-[2-Hydroxy-3-(2-cyano-4-(2-carboethoxyethyl) phenoxy)propyl]-1,1-dimethyl-2-(2-naphthyl) ethylamine;

(R)-N-[2-Hydroxy-3-(2-cyano-4-(2-carboxyethyl) phenoxy)propyl]-1,1-dimethyl-2-(2-naphthyl) ethylamine;

(R)-N-[2-Hydroxy-3-(2-cyano-5-(3-carbethoxypropyl) phenoxy)propyl]-1,1-dimethyl-2-(2-naphthyl) ethylamine;

(R)-N-[2-Hydroxy-3-(2-cyano-5-(3-carboxypropyl) phenoxy)propyl]-1,1-dimethyl-2-(2-naphthyl) ethylamine;

(R)-N-[2-Hydroxy-3-(2-cyano-5-(2-carbethoxyethyl) phenoxy)propyl]-1,1-dimethyl-2-(2-naphthyl) ethylamine;

(R)-N-[2-Hydroxy-3-(2-cyano-5-(2-carboxyethyl) phenoxy)propyl]-1,1-dimethyl-2-(2-naphthyl) ethylamine;

(R)-N-[2-Hydroxy-3-(2-cyano-4-(3-carbethoxypropyl) phenoxy)propyl]-1,1-dimethyl-2-(2-naphthyl) ethylamine;

(R)-N-[2-Hydroxy-3-(2-cyano-4-(3-carboxypropyl) phenoxy)propyl]-1,1-dimethyl-2-(2-naphthyl) ethylamine:

(R)-N-[2-Hydroxy-3-(2-cyano-3-(3-carbethoxypropyl) phenoxy)propyl]-1,1-dimethyl-2-(2-naphthyl) ethylamine;

(R)-N-[2-Hydroxy-3-(2-cyano-3-(3-carboxypropyl) phenoxy)propyl]-1,1-dimethyl-2-(2-naphthyl) ethylamine;

(R)-N-[2-Hydroxy-3-(2-cyano-3-(2-carbethoxyethyl) phenoxy)propyl]-1,1-dimethyl-2-(2-naphthyl) ethylamine;

(R)-N-[2-Hydroxy-3-(2-cyano-3-(2-carboxyethyl) phenoxy)propyl]-1,1-dimethyl-2-(2-naphthyl) ethylamine;

(R)-N-[2-Hydroxy-3-(2-cyano-4-(carbethoxymethyl) phenoxy)propyl]-1,1-dimethyl-2-(2-naphthyl) ethylamine;

(R)-N-[2-Hydroxy-3-(2-cyano-4-(carboxymethyl) phenoxy)propyl]-1,1-dimethyl-2-(2-naphthyl) ethylamine;

(R)-N-[2-Hydroxy-3-(2-cyano-5-(carbethoxymethyl) phenoxy)propyl]-1,1-dimethyl-2-(2-naphthyl) ethylamine;

(R)-N-[2-Hydroxy-3-(2-cyano-5-(carboxymethyl) phenoxy)propyl]-1,1-dimethyl-2-(2-naphthyl) ethylamine;

(R)-N-[2-Hydroxy-3-(2-cyano-4-(2-carbethoxy-trans-ethylene)phenoxy)propyl]-1,1-dimethyl-2-(2-naphthyl)ethylamine;

(R)-N-[2-Hydroxy-3-(2-cyano-4-(2-carboxy-trans-ethylene)phenoxy)propyl]-1,1-dimethyl-2-(2-naphthyl)ethylamine;

(R)-1-[1,1-dimethyl-2-(2-naphthyl)ethylamino]-3-[(3-(2-aminophenoxy)-4-methoxycarbonyl)phenoxy]-propan-2-ol; and and pharmaceutically acceptable salts and complexes thereof.

Pharmaceutically acceptable salts are non-toxic salts in the amounts and concentrations at which they are administered.

Pharmaceutically acceptable salts include acid addition salts such as those containing sulfate, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. A preferred salt is a hydrochloride. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present.

The present invention provides compounds of Formula (I) above which can be prepared using standard techniques. An overall strategy for preparing preferred compounds described herein can be carried out as described in this section. The examples which follow illustrate the synthesis of specific compounds. Using the protocols described herein as a model, one of ordinary skill in the art can readily produce other compounds of the present invention.

All reagents and solvents were obtained from commercial vendors. Starting materials (e.g., amines and epoxides) were synthesized using standard techniques and procedures.

Scheme 1

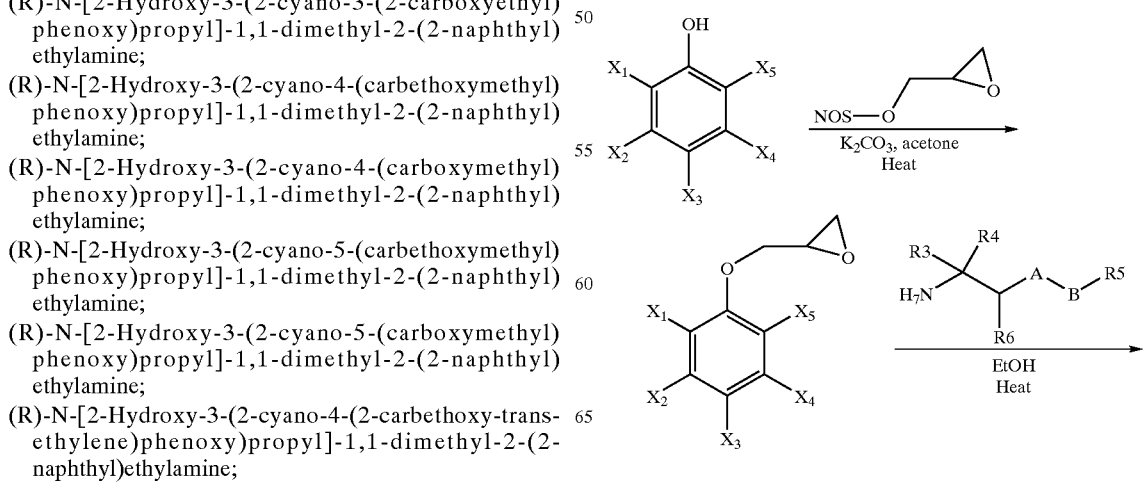

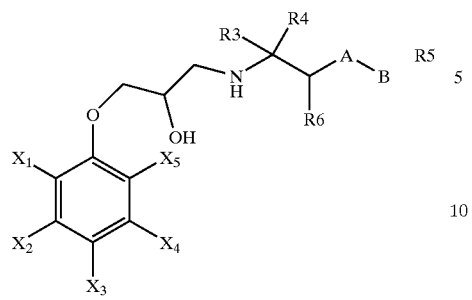
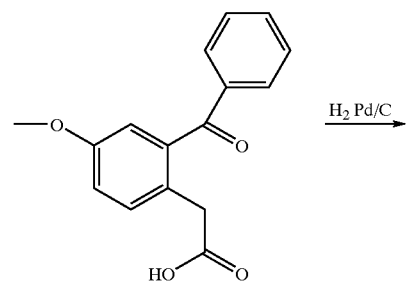
Scheme 2
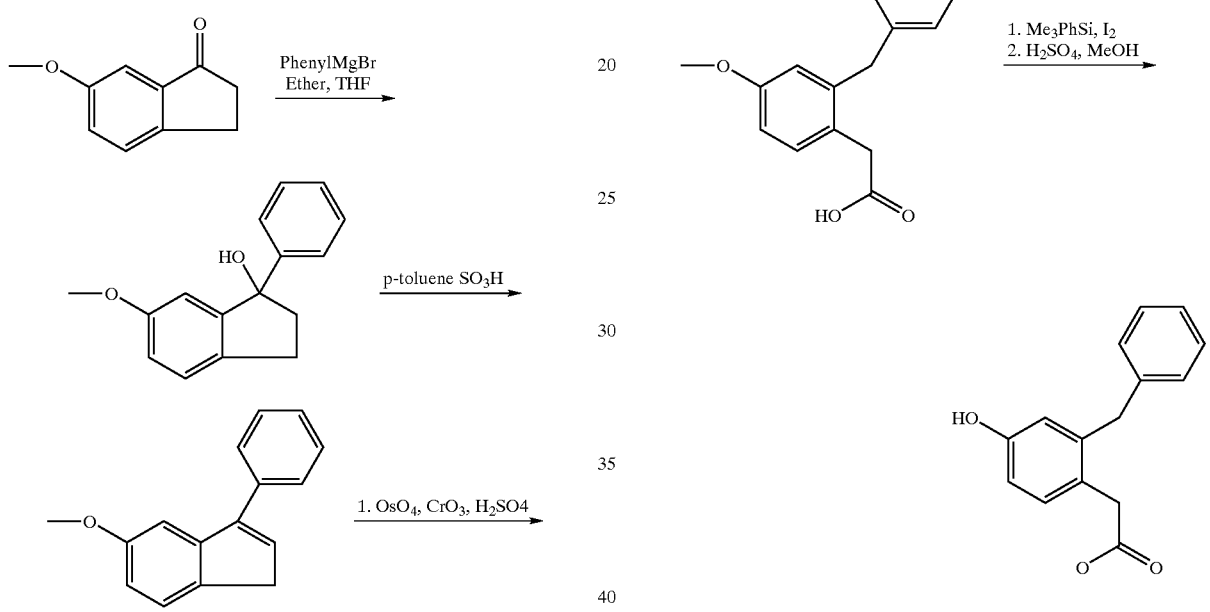
Scheme 3
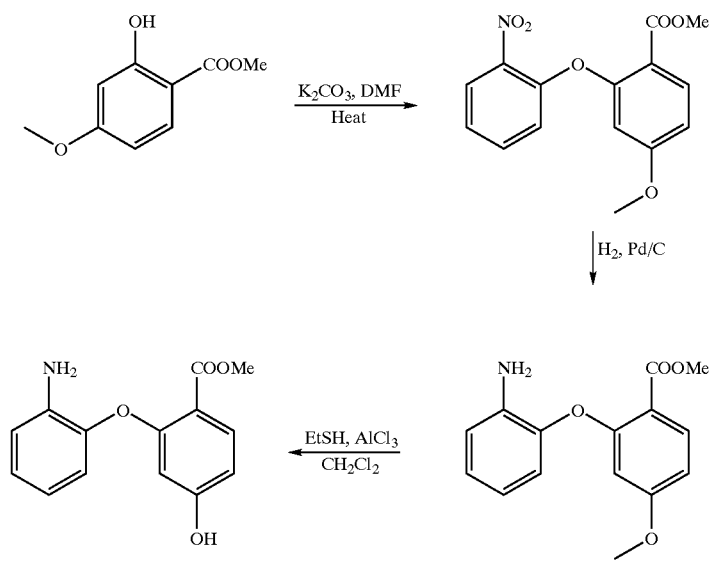

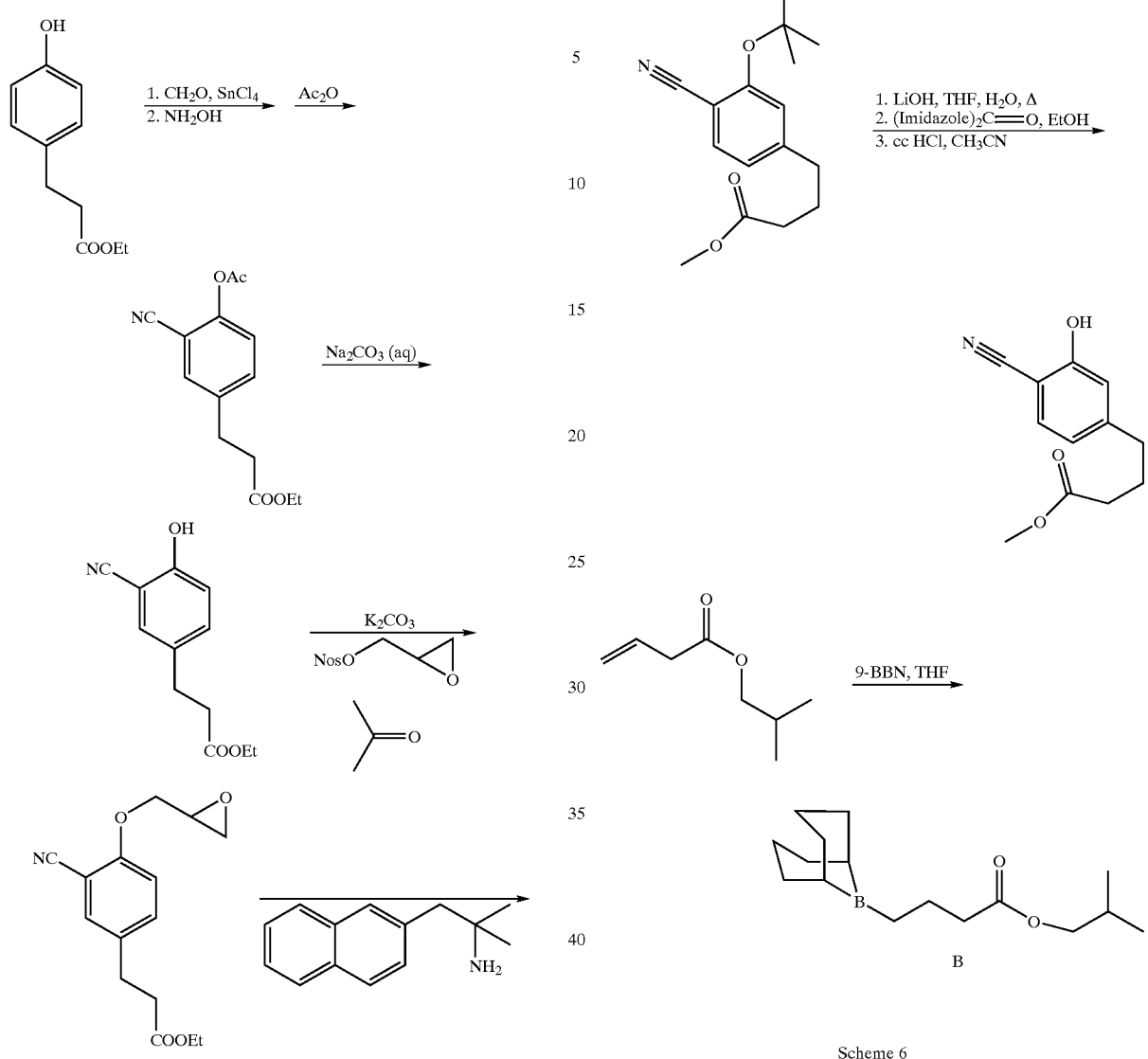
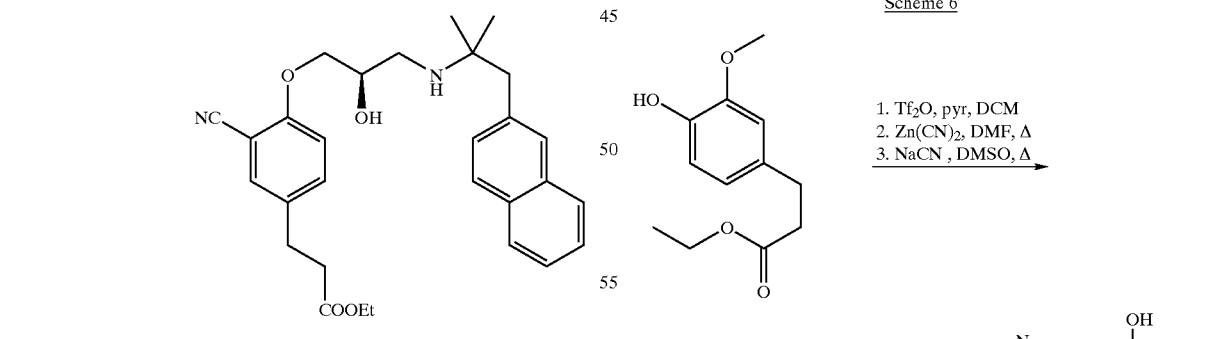
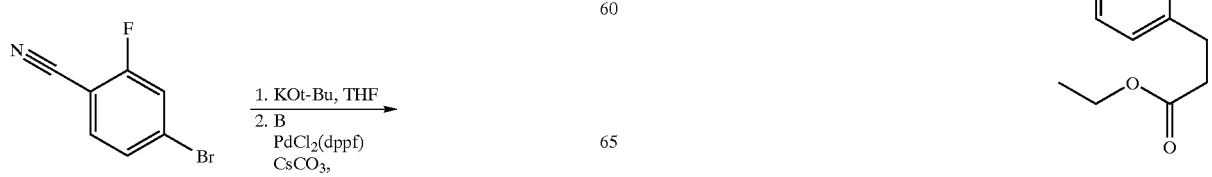

Scheme 7

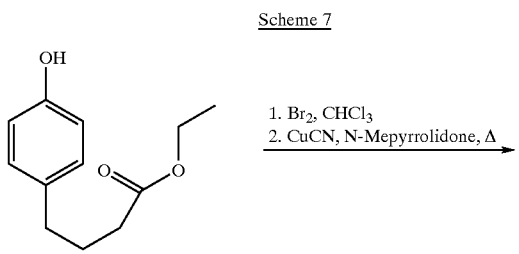

Scheme 8

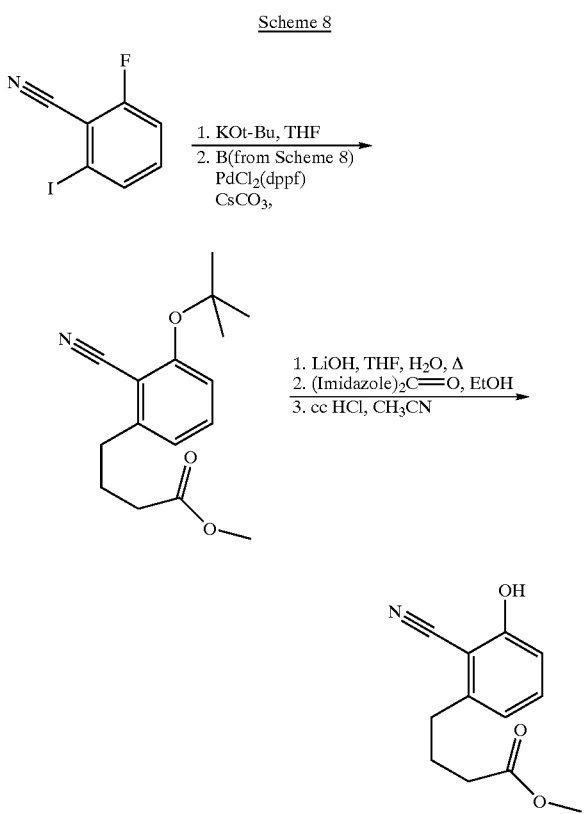

Scheme 9

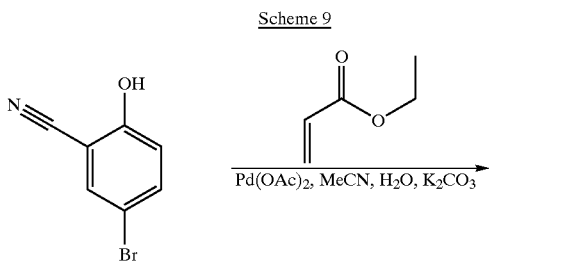

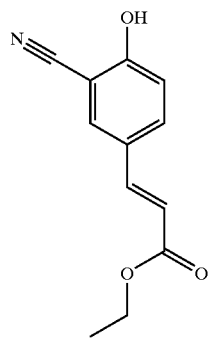

General Preparation

A general procedure used to synthesize many of the compounds can be carried out as described in Scheme 1: a solution of aryl alcohol in acetone was treated with an appropriate base such as $K_2CO_3$, heated for 15 min. R-glycidyl nosylate was added and the reaction continued overnight to give the corresponding glycidyl ether. In the case of an alkyl alcohol (e.g., $Y_3$ is $C_{1-4}$ alkylene-O), a stronger base, e.g. NaH in DMF was used. This method can also be used for aryl alcohols. A solution of the substituted glycidyl ether and excess amine (typically 1,1-dimethyl-2-(4-methyloxyphenyl)ethylamine) in absolute ethanol, acetonitrile, THF or any other similar solvent in the presence of a suitable catalyst such as $LiClO_4$ is stirred overnight at reflux. The product is purified by normal phase chromatography. Hydrochloride salts are prepared by treatment of the corresponding free base with HCl either in gas phase or 4M dioxane solution, or any other standard method. A method for preparing methyl 2-(2-benzyl-4-hydroxy)phenylacetates is outlined in Scheme 2. Grignard addition followed by dehydration and oxidative cleavage of the resulting double bond yields the benzophenone derivative which is deoxygenated and demethylated to give the aryl alcohol acid and its corresponding ester. A method for preparing 1-(2-aminophenoxy)-2-methoxycarbonyl-5-hydroxy-benzenes is outlined in Scheme 3. Displacement of the aryl fluoride gave the biphenyl ether. Reduction of the nitro group followed by cleavage of the methyl ether gave the desired aryl alcohol. Schemes 4–9 outlines the general synthesis of the corresponding phenol substituted with the different propionic and butiric acid/esters side chains, with appropriate manipulation and protection of any chemical functionality, synthesis of the remaining compounds of Formula (I) is accomplished by methods analogous to those above and to those described in the Experimental section.

In order to use a compound of Formula (I) or a pharmaceutically acceptable salt thereof for the treatment of humans and other mammals, it is normally formulated in accordance with standard pharmaceutical practice as a pharmaceutical composition.

The calcilytic compounds can be administered by different routes including intravenous, intraperitoneal, subcutaneous, intramuscular, oral, topical (transdermal), or transmucosal administration. For systemic administration, oral administration is preferred. For oral administration, for example, the compounds can be formulated into conventional oral dosage forms such as capsules, tablets, and liquid preparations such as syrups. elixirs, and concentrated drops.

Alternatively, injection (parenteral administration) may be used, e.g., intramuscular, intravenous, intraperitoneal, and subcutaneous. For injection, the compounds of the invention are formulated in liquid solutions, preferably, in physiologically compatible buffers or solutions, such as saline solution, Hank's solution, or Ringer's solution. In addition, the compounds may be formulated in solid form and redissolved or suspended immediately prior to use. Lyophilized forms can also be produced.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays, rectal suppositories, or vaginal suppositories.

For topical administration, the compounds of the invention can be formulated into ointments, salves, gels, or creams, as is generally known in the art.

The amounts of various calcilytic compounds to be administered can be determined by standard procedures taking into account factors such as the compound $IC_{50}$, $EC_{50}$, the biological half-life of the compound, the age, size and weight of the patient, and the disease or disorder associated with the patient. The importance of these and other factors to be considered are known to those of ordinary skill in the art.

Amounts administered also depend on the routes of administration and the degree of oral bioavailability. For example, for compounds with low oral bioavailability, relatively higher doses will have to be administered.

Preferably the composition is in unit dosage form. For oral application, for example, a tablet, or capsule may be administered, for nasal application, a metered aerosol dose may be administered, for transdermal application, a topical formulation or patch may be administered and for transmucosal delivery, a buccal patch may be administered. In each case, dosing is such that the patient may administer a single dose.

Each dosage unit for oral administration contains suitably from 0.01 to 500 mg/Kg, and preferably from 0.1 to 50 mg/Kg, of a compound of Formula (I) or a pharmaceutically acceptable salt thereof, calculated as the free base. The daily dosage for parenteral, nasal, oral inhalation, transmucosal or transdermal routes contains suitably from 0.01 mg to 100 mg/Kg, of a compound of Formula(I). A topical formulation contains suitably 0.01 to 5.0% of a compound of Formula (I). The active ingredient may be administered, for example, from 1 to 6 times per day, preferably once, sufficient to exhibit the desired activity, as is readily apparent to one skilled in the art.

As used herein, "treatment" of a disease includes, but is not limited to prevention, retardation and prophylaxis of the disease.

Diseases and disorders which might be treated or prevented, based upon the affected cells, include bone and mineral-related diseases or disorders; hypoparathyroidism; those of the central nervous system such as seizures, stroke, head trauma, spinal cord injury, hypoxia-induced nerve cell damage, such as occurs in cardiac arrest or neonatal distress, epilepsy, neurodegenerative diseases such as Alzheimer's disease, Huntington's disease and Parkinson's disease, dementia, muscle tension, depression, anxiety, panic disorder, obsessive-compulsive disorder, post-traumatic stress disorder, schizophrenia, neuroleptic malignant syndrome, and Tourette's syndrome; diseases involving excess water reabsorption by the kidney, such as syndrome of inappropriate ADH secretion (SIADH). cirrhosis, congestive heart failure, and nephrosis; hypertension; preventing and/or decreasing renal toxicity from cationic antibiotics (e.g., aminoglycoside antibiotics); gut motility disorders such as diarrhea and spastic colon; GI ulcer diseases; GI diseases with excessive calcium absorption such as sarcoidosis; autoimmune diseases and organ transplant rejection: squamous cell carcinoma; and pancreatitis.

In a preferred embodiment of the present invention, the present compounds are used to increase serum parathyroid hormone ("PTH") levels. Increasing serum PTH levels can be helpful in treating diseases such as hypoparathyroidism, osteosarcoma, periodontal disease, fracture, osteoarthritis, rheumatoid arthritis, Paget's disease, humoral hypercalcemia malignancy and osteoporosis.

Another aspect of the present invention describes a method of treating a patient comprising administering to the patient an amount of a present compound sufficient to increase the serum PTH level. Preferably, the method is carried out by administering an amount of the compound effective to cause an increase in duration and/or quantity of serum PTH level sufficient to have a therapeutic effect.

In various embodiments, the compound administered to a patient causes an increase in serum PTH having a duration of up to one hour, about one to about twenty-four hours, about one to about twelve hours, about one to about six hours, about one to about five hours, about one to about four hours, about two to about five hours, about two to about four hours, or about three to about six hours.

In an altemattive embodimenf of the present invention, the compound administered to a patient causes an increase in serum PTH having a duration of more than about twenty four hours provided that it is co-administered with an anti resorptive agent.

In additional different embodiments, the compound administered to a patient causes an increase in serum PTH of up to two fold, two to five fold, five to ten fold, and at least 10 fold, greater than peak serum PMN in the patient. The peak serum level is measured with respect to a patient not undergoing treatment.

Composition of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

No unacceptable toxological effects are expected when compounds of the present invention are administered in accordance with the present invention.

The biological activity of the compounds of Formula (I) are demonstrated by the following tests:

(I) Calcium Receptor Inhibitor Assay

Calcilytic activity was measured by determining the $IC_{50}$ of the test compound for blocking increases of intracellular $Ca^{2+}$ elicited by extracellular $Ca^{2+}$ in HEK 293 4.0–7 cells stably expressing the human calcium receptor. HEK 293 4.0–7 cells were constructed as described by Rogers et al., *J. Bone Miner. Res.* 10 Suppl. 1:S483, 1995 (hereby incorporated by reference herein). Intracellular $Ca^{2+}$ increases were elicited by increasing extracellular $Ca^{2+}$ from 1 to 1.75 mM. Intracellular $Ca^{2+}$ was measured using fluo-3, a fluorescent calcium indicator.

The procedure was as follows:

1. Cells were maintained in T-150 flasks in selection media (DMEM supplemented with 10% fetal bovine serum and 200 ug/mL hygromycin B), under 5% $CO_2$:95% air at 37° C. and were grown up to 90% confluency.

2. The medium was decanted and the cell monolayer was washed twice with phosphate-buffered saline (PBS) kept at 37° C. After the second wash, 6 mL of 0.02% EDTA in PBS was added and incubated for 4 minutes at 37° C. Following the incubation, cells were dispersed by gentle agitation.

3. Cells from 2 or 3 flasks were pooled and pelleted (100×g). The cellular pellet was resuspended in 10–15 mL of SPF-PCB+ and pelleted again by centrifugation. This washing was done twice.

Sulfate- and phosphate-free parathyroid cell buffer (SPF-PCB) contains 20 mM Na-Hepes, pH 7.4, 126 mM NaCl, 5 mM KCl, and 1 mM $MgCl_2$. SPF-PCB was made up and stored at 4° C. On the day of use, SPF-PCB was supplemented with 1 mg/mL of D-glucose and 1 mM $CaCl_2$ and then split into two fractions. To one fraction, bovine serum albumin (BSA; fraction V, ICN) was added at 5 mg/mL (SPF-PCB+). This buffer was used for washing, loading and maintaining the cells. The BSA-free fraction was used for diluting the cells in the cuvette for measurements of fluorescence.

4. The pellet was resuspended in 10 mL of SPF-PCB+ containing 2.2 uM fluo-3 (Molecular Probes) and incubated at room temperature for 35 minutes.

5. Following the incubation period, the cells were pelleted by centrifugation. The resulting pellet was washed with SPF-PCB+. After this washing, cells were resuspended in SPF-PCB+ at a density of 1–2×106 cells/mL.

6. For recording fluorescent signals, 300 uL of cell suspension were diluted in 1.2 mL of SPF buffer containing 1 mM $CaCl_2$ and 1 mg/mL of D-glucose. Measurements of fluorescence were performed at 37° C. with constant stirring using a spectrofluorimeter. Excitation and emission wavelengths were measured at 485 and 535 nm, respectively. To calibrate fluorescence signals, digitonin (5 mg/mL in ethanol) was added to obtain Fmax, and the apparent Fmin was determined by adding Tris-EGTA (2.5 M Tris-Base, 0.3 M EGTA). The concentration of intracellular calcium was calculated using the following equation:

$$\text{Intracellular calcium} = (F - F_{min}/F_{max}) \times K_d; \text{ where } K_d = 400 \text{ nM.}$$

7. To determine the potential calcilytic activity of test compounds, cells were incubated with test compound (or vehicle as a control) for 90 seconds before increasing the concentration of extracellular $Ca^{2+}$ from 1 to 2 mM. Calcilytic compounds were detected by their ability to block, in a concentration-dependent manner, increases in the concentration of intracellular $Ca^{2+}$ elicited by extracellular $Ca^{2+}$.

In general, those compounds having lower $IC_{50}$ values in the Calcium Receptor Inhibitor Assay are more preferred compounds. Compounds having an $IC_{50}$ greater than 50 uM were considered to be inactive. Preferred compounds are those having an $IC_{50}$ of 10 uM or lower, more preferred compounds have an $IC_{50}$ of 1 uM, and most preferred compounds have an $IC_{50}$ of 0.1 uM or lower.

(II) Calcium Receptor Binding Assay

HEK 293 4.0–7 cells stably transfected with the Human Parathyroid Calcium Receptor("HuPCaR") were scaled up in T180 tissue culture flasks. Plasma membrane is obtained by polytron homogenization or glass douncing in buffer (50 mM Tris-HCl pH 7.4, 1 mM EDTA, 3 mM $MgCl_2$) in the presence of a protease inhibitor cocktail containing 1 uM Leupeptin, 0.04 uM Pepstatin, and 1 mM PMSF. Aliquoted membrane was snap frozen and stored at –80° C. $^3H$ labeled compound was radiolabeled to a radiospecific activity of 44Ci/mmole and was aliquoted and stored in liquid nitrogen for radiochemical stability.

A typical reaction mixture contains 2 nM $^3H$ compound ((R,R)-N-4'-Methoxy-t-3-3'-methyl-1'-ethylphenyl-1-(1-naphthyl)ethylamine), or $^3H$ compound (R)-N-[2-Hydroxy-3-(3-chloro-2-cyanophenoxy)propyl]-1,1-dimethyl-2-(4-methoxyphenyl)ethylamine 4–10 ug membrane in homogenization buffer containing 0.1% gelatin and 10% EtOH in a reaction volume of 0.5 mL. Incubation is performed in 12×75 polyethylene tubes in an ice water bath. To each tube 25 uL of test sample in 100% EtOH is added, followed by 400 uL of cold incubation buffer, and 25 uL of 40 nM $^3H$-compound in 100% EtOH for a final concentration of 2 nM. The binding reaction is initiated by the addition of 50 uL of 80–200 ug/mL HEK 293 4.0–7 membrane diluted in incubation buffer, and allowed to incubate at 4° C. for 30 min. Wash buffer is 50 mM Tris-HCl containing 0.1% PEI. Nonspecific binding is determined by the addition of 100-fold excess of unlabeled homologous ligand, and is generally 20% of total binding. The binding reaction is terminated by rapid filtration onto 1% PEI pretreated GF/C filters using a Brandel Harvestor. Filters are placed in scintillation fluid and radioactivity assessed by liquid scintillation counting.

The following examples are illustrative, but not limiting of the embodiments of the present invention.

EXAMPLE 1

Preparation of (R)-1-[1,1-dimethyl-2-(4-methoxyphenyl)ethylamino]-3(4-(2-phenyl-2-R,S-methoxycarbonylethyl))phenoxy]-propan-2-ol Hydrochloride Salt a) (R) 4-(2-Phenyl-2-R,S-(methoxycarbonyl)ethyl)-phenoxyglycidol The material purchased from Sigma, 3-(p-hydroxyphenyl) 2-phenylpropionic acid, (1 g, 4.1 mmol) was dissolved in methanol (10 mL) and was treated with concentrated $H_2SO_4$ (0.5 mL) at reflux for 16 h. The mixture was cooled, evaporated, taken up in 5% $NaHCO_3$ and extracted into diethyl ether. A mixture of this crude compound (1 g, 4.1 mmol), $K_2CO_3$ (0.62 g, 4.5 mmol), and 2R-(−)-glycidyl-3-nitrobenzenesulfonate (1.6 g, 6.2 mmol) in acetone (50 mL) was refluxed for 24 h. The mixture was cooled, concentrated, taken up in H₂O, extracted with EtOAc. The organic extracts were washed with 5% NaHCO₃, brine, dried over MgSO₄, filtered, concentrated and purified by flash column chromatography (50% EtOAc/Hexane) to afford the title compound (1 g, 75%) as an off white foam. $^1$H-NMR (250 MHz, CDCl₃): δ 2.70–2.73 (m, 1H), 2.85–2.99 (m, 2H), 3.29–3.35 (m, 2H), 3.38 (s, 3H), 3.76–3.90 (m, 2H), 4.15 (dd, j=5.4, 11.4 Hz, 1H), 6.78 (d, J=9.1 Hz, 2H, 7.01 (d, J=9.3 Hz, 2H), 7.23–7.29 (m, 5H).

b) (R) 1-[1,1-Dimethyl-2-(4-methoxyphenyl)ethylamino]-3 (4-(2-phenyl-2-R,S-methoxycarbonylethyl))phenoxy]-propan-2-ol Hydrochloride Salt A mixture of the compound of Example 1(a) (0.3 g, 0.96 mmol), and 4-methoxyphenyl-1,1-dimethyl ethylamine (0.2 g, 1.06 mmol) in ethanol (20 mL) was heated at reflux for 24 h. The mixture was cooled, concentrated and purified by flash column chromatography (3% MeOH/CHCl₃) to afford as a colorless oil (0.321 g, 69%) which (0.200 g) was stirred in methanol and added 4M HCl, concentrated and triturated in ether to give the title compound (0.325 g). ESMS (M+H)⁺ m/e 492.4.

EXAMPLE 2

Preparation of (R)-1-[1,1-Dimethyl-2-(4-methoxyphenyl)ethylamino]-3-[(4-(2-phenyl-2-R,S-carboxyethyl))phenoxy]-propan-2-ol Hydrochloride Salt The remaining material from Example 1 (b) (0.13 g, 0.28 mmol) was dissolved in methanol (5 mL) and was treated with 1M NaOH aq (1.2 mL) at room temperature for 16 h. The reaction was quenched with 1M HCl, extracted with CHCl₃, dried with MgSO₄, filtered and evaporated to afford a white powder (0.12 g). ESMS (M+H)⁺ m/e; 478.4.

EXAMPLE 3

Preparation of (R)-1-[1,1-Dimethyl-2-(4-methoxyphenyl)ethylamino]-3-[(3-benzyl-4-methoxycarbonylmethyl)phenoxy]-propan-2-ol Hydrochloride Salt a) 2-Benzyl-4-methoxyphenylacetic Acid A solution of 2-benzoyl-4-methoxyphenylacetic acid (5.18 g, 20.3 mmol), prepared by the method of *J. Med. Chem.* 1981, 24, 998, in glacial acetic acid (200 mL) was treated under argon with 10% Pd/C (1 g) and hydrogenated at 50 psi for 17 h. The mixture was filtered using celite and the filtrate concentrated and chased with toluene and methylene chloride to give the title compound (4.3 g). $^1$H-NMR (350 MHz, CDCl₃): δ 3.52 (s, 2H), 3.75 (s, 3H), 4.0 (s, 2H), 6.7 (m, 2H). 7.15 (m, 6H).

b) Methyl 2-(2-Benzyl-4-hydroxy)phenylacetate

A mixture of the compound of Example 3 (a) (0.50 g, 1.9 mmol), PhSiMe₃ (5 mL), and iodine (0.99 g, 7.8 mmol) was heated at 130° C. for 16 h. The mixture was cooled, added saturated NaHSO₃ aq and extracted with EtOAc. The organic extracts were washed with H₂O, brine, dried over MgSO₄, filtered concentrated, dissolved in methanol (10 mL) and treated with concentrated sulfuric acid (1 mL) at reflux for 16 h. The material was evaporated, quenched with NaHCO₃ and extracted with ether to give the title compound (0.673 g). $^1$H-NMR (250 MHz, CDCl₃): δ 3.52 (s, 2H), 3.59 (s, 3H), 3.94 (s, 2H) 6.56–7.25 (m, 8H).

c) (R)-Methyl 2-(2-Benzyl-4-glycidyl)phenylacetate

A mixture of the compound of Example 3 (b) ( 2 mmol), K₂CO₃ (0.39 g, 2.8 mmol), and 2 R-(−)-glycicyl -3-nitrobenzenesulfonate (0.73 g, 2.8 mmol) in acetone (20 mL) was refluxed for 16 h. The mixture was cooled, concentrated, taken up in H₂O, extracted with ether and purified by flash column chromatography (25% EtOAc/Hexane) to afford the title compound (0.232 g) as a clear oil. $^1$H-NMR (250 MHz, CDCl3): δ 2.70–2.73 (m, 1H), 2.85–2.89 (m, 1H), 3.30–3.32 (m, 1H), 3.53 (s , 2H), 3.59 (s, 3H), 3.87–3.94 (m, 1H), 3.98 (s, 2H), 4.18 (dd, J=5.4, 11.4 Hz, 1H), 6.70–7.29 (m, 8H).

d) (R)-1-[1,1-Dimethyl-2-(4-methoxyphenyl)ethylamino]-3-[(3-benzyl-4-methoxycarbonylmethyl)phenoxy]-propan-2-ol Hydrochloride Salt A mixture of the compound of Example 3(c) (0.37 mmol), and 4-methoxyphenyl-1,1-dimethylethylamine (0.2 g, 1.11 mmol) in ethanol (20 mL) was heated at reflux for 24 h. The mixture was cooled, concentrated and purified by flash column chromatography (5% MeOH/CHCl₃) to afford as a colorless oil (0.110 g) which (0.020 g) was stirred in methanol and added 4M HCl, concentrated and triturated in ether to give the title compound (0.020 g). ESMS (M+H)⁺ m/e 492.3.

EXAMPLE 4

Preparation of (R)-1-[1,1-Dimethyl-2-(2-naphthyl) ethylamino]-3-[(3-benzyl-4-methoxycarbonylmethyl)phenoxy]-propan-2-ol Hydrochloride Salt A mixture of the compound of Example 3(c) (0.37 mmol), and 2-naphthylphenyl-1,1-dimethyl ethylamine (0.22 g, 1.12 mmol) in ethanol (20 mL) was heated at reflux for 24 h. The mixture was cooled, concentrated and purified by flash column chromatography (5% MeOH/CHCl₃) to afford as a colorless oil (0.100 g) which (0.020 g) was stirred in methanol and added 4M HCl, concentrated and triturated in ether to give the title compound (0.025 g). ESMS (M+H)⁺ m/e 512.4.

EXAMPLE 5

Preparation of (R)-1-[1,1-Dimethyl-2-(2-naphthyl) ethylamino]-3-[(3-benzyl-4-carboxymethyl) phenoxy]-propan-2-ol Hydrochloride Salt A mixture of the compound of Example 4 (0.151 mmol), and 1M NaOH (0.200 mL), was dissolved in methanol (2 mL) and stirred for 24 h. The reaction was quenched with 1M HCl, extracted with CHCl₃, dried with MgSO₄, filtered and evaporated to afford a white powder (0.05 g). ESMS (M+H)⁺ m/e 498.3.

EXAMPLE 6

Preparation of (R)-1-[1,1-Dimethyl-2-(4-methoxyphenyl)ethylamino]-3-[(3-benzyl-4-carboxymethyl)phenoxy]-propan-2-ol Hydrochloride Salt A mixture of the compound of Example 3 (0.173 mmol), and 1M NaOH (2.0 mL), was dissolved in methanol (5 mL) and stirred for 48 h. The reaction was quenched with 1M HCl, extracted with CHCl₃, dried with MgSO₄, filtered and evaporated to afford a white powder (0.03 g). ESMS (M+H)⁺ m/e 478.3.

EXAMPLE 7

Preparation of (R)-1-[1,1-Dimethyl-2-(4-methoxyphenyl)ethylamino]-3-[(4-(3-hydroxy) propyl)phenoxy]-propan-2-ol Hydrochloride Salt A mixture of 3-p-hydroxyphenylpropanol (Aldrich, 1 g, 6.5 mmol), K₂CO₃ (1.1 g, 7.8 mmol), and 2R-(−)-glycidyl- 3-nitrobenzenesulfonate (2.1 g, 8.2 mmol) in acetone (30 mL) was refluxed for 24 h. The mixture was cooled, concentrated, taken up in H$_2$O and extracted with diethyl ether. The organic extracts were washed with 5% NaHCO$_3$, brine, dried over MgSO$_4$, filtered, and concentrated. This compound (0.35 g, 1.68 mmol), and 4-methoxyphenyl-1,1-dimethyl ethylamine (0.331 g, 1.89 mmol) in ethanol (10 mL) was heated at reflux for 24 h. The mixture was cooled, concentrated and purified by flash column chromatography (5% MeOH/CHCl$_3$) to afford an oil which was stirred in methanol and added 4M HCl, concentrated and triturated in ether to give a white powder of the title compound (0.15 g). ESMS (M+H)$^+$ m/e 388.3.

EXAMPLE 8

Preparation of (R)-1-[1,1-Dimethyl-2-(4-methoxyphenyl)ethylamino]-3-[(4-(2-hydroxy)ethyl)phenoxy]-2-propan-2-ol Hydrochloride Salt A mixture of 4-hydroxyphenylethyl alcohol (Aldrich, 1 g, 7.25 mmol), K$_2$CO$_3$ (1.2 g, 8.7 mmol), and 2R-(–)-glycidyl-3-nitrobenzenesulfonate (2.07 g, 8.0 mmol) in acetone (30 mL) was refluxed for 24 h. The mixture was cooled, concentrated, taken up in H$_2$O and extracted with diethyl ether. The organic extracts were washed with 5% NaHCO$_3$, brine, dried over MgSO$_4$, filtered, and concentrated. This compound (0.394 g, 2.03 mmol), and 4-methoxyphenyl-1,1-dimethyl ethylamine (0.400 g, 2.23 mmol) in ethanol (10 mL) was heated at reflux for 24 h. The mixture was cooled, concentrated and purified by flash column chromatography (5% MeOH/CHCl$_3$) to afford an oil which was stirred in methanol and added 4M HCl, concentrated and triturated in ether to give the title compound as a white powder of (0.11 g). ESMS (M+H)$^+$ m/e 374.4.

EXAMPLE 9

Preparation of (R)-1-[1,1-Dimethyl-2(4-methoxyphenyl)ethylamino]-3-[(4-(2-cyano)ethyl)phenoxy]-propan-2-ol Hydrochloride Salt A mixture of 4-hydroxyphenyl propionitrile (Lancasater, 1 g, 6.8 mmol), K$_2$CO$_3$ (2.8 g, 20.4 mmol), and 2R-(–)-glycidyl-3-nitrobenzenesulfonate (1.76 g, 6.8 mmol) in acetone (30 mL) was refluxed for 24 h. The mixture was cooled, concentrated, taken up in H$_2$O and extracted with diethyl ether. The organic extracts were washed with 5% NaHCO$_3$, brine, dried over MgSO$_4$, filtered, and concentrated. This compound (0.28 g, 1.38 mmol), and 4-methoxyphenyl-1,1-dimethyl ethylamine (0.272 g, 1.52 mmol) in ethanol (5 mL) was heated at reflux for 24 h. The mixture was cooled, concentrated and purified by flash column chromatography (5% MeOH/CHCl$_3$) to afford an oil which was stirred in methanol and added 4M HCl, concentrated and triturated in ether to give the title compound as a white powder (0.25 g). ESMS (M+H)$^+$ m/e 483.3.

EXAMPLE 10

Preparation of (R)-Methyl 2-[4-[3-[2-(4-methoxyphenyl)-1,1-dimethylethylamino]-2-hydroxypropoxy]benzoylbenzoate Hydrochloride Salt a) (R)-Methyl 4-(oxiranylmethoxy)phenylbenzoyl)benzoic Ester The material purchased from ICN, 2-(4-hydroxybenzoyl) benzoic acid, (3.5 g, 14.5 mmol) was dissolved in methanol (50 mL) and was treated with concentrated H$_2$SO$_4$ (0.5 mL) at reflux for 16 h. The mixture was cooled, evaporated, taken up in 5% NaHCO$_3$ and extracted into diethyl ether. A mixture of this crude compound (3.07 g, 11.99 mmol), K$_2$CO$_3$ (4.97 g, 36 mmol), and 2R-(–)-glycidyl-3-nitrobenzenesulfonate (3.2 g, 11.99 mmol) in acetone (50 mL) was refluxed for 24 h. The mixture was cooled, concentrated, takenup in H$_2$O, extracted with EtOAc. The organic extracts were washed with saturated NaHCO$_3$, brine, dried over MgSO$_4$, filtered, concentrated and purified by flash column chromatography (50% EtOAc/Hexane) to afford the title compound (3.48 g) as an off white foam. $^1$H-NMR (250 MHz, CDCl3): δ 2.70–2.73 (m, 1H), 2.91–2.99 (m, 1H), 3.32–3.45 (m, 1H), 3.61 (s, 3H), 3.91–3.99 (m, 1H), 4.35 (dd, J=5.3, 11.4 Hz, 1H), 6.80–8.0 (m, 8H).

b) (R)-Methyl 2-[4-[3-[2-(4-methoxyphenyl)-1,1-dimethylethylamino]-2-hydroxypropoxy]benzoylbenzoate Hydrochloride Salt A mixture of the compound from Example 10 (a) (1.75 g, 6.25 mmol), and 4-methoxyphenyl-1,1-dimethyl ethylamine (1.11 g, 6.25 mmol) in ethanol (5 mL) was heated at reflux for 16 h. The mixture was cooled, concentrated and purified by flash column chromatography (5% MeOH/CHCl$_3$) to afford an oil (1.27 g) of which (0.384 g) was stirred in methanol and added 4M HCl, concentrated and triturated in ether to give the title compound as a white powder (0.28 g). ESMS (M+H)$^+$ m/e 492.0.

EXAMPLE 11

Preparation of (R)-2-[4-[3-[2-(4-Methoxyphenyl)-1,1-dimethylethylamino]-2-hydroxypropoxy]benzoylbenzoic Acid Hydrochloride Salt A mixture of the compound of Example 10 (b)(0.30 g, 0.61 mmol), and 1M NaOH (1 mL), was dissolved in methanol (5 mL) and stirred at rt for 12 h then reflux for 5 h. The reaction was quenched with 1M HCl, extracted with CHCl$_3$, dried with MgSO$_4$, filtered and evaporated to afford a white powder (0.125 g). ESMS (M+H)$^+$ m/e 487.1.

EXAMPLE 12

Preparation of (R)-1-[1,1-Dimethyl-2-(4-methoxyphenyl)ethylamino]-3-[(4-cyanomethyl)phenoxy]-propan-2-ol Hydrochloride Salt A mixture of 4-hydroxybenzylcyanide (Aldrich, 1 g, 7.51 mmol), K$_2$CO$_3$ (3.1 g, 22 mmol), and 2R-(–)-glycidyl-3-nitrobenzenesulfonate (1.95 g, 7.51 mmol) in acetone (25 mL) was refluxed for 16 h. The mixture was cooled, concentrated, taken up in H$_2$O and extracted with diethyl ether. The organic extracts were washed with 5% NaHCO$_3$, brine, dried over MgSO$_4$, filtered, and concentrated. This compound (0.250 g, 1.3 mmol), and 4-methoxyphenyl-1,1-dimethyl ethylamine (0.255 g, 1.43 mmol) in ethanol (10 mL) was heated at reflux for 16 h. The mixture was cooled, concentrated and purified by flash column chromatography (5% MeOH/CHCl$_3$) to afford an oil which was stirred in methanol and added 4M HCl, concentrated and triturated in ether to give the title compound as a white powder (0.100 g). ESMS (M+H)$^+$ m/e 369.1.

EXAMPLE 13

Preparation of (R)-1-[1,1-Dimethyl-2-(4-methoxyphenyl)ethylamino]-3-[(4-cyano)phenoxy]-propan-2-ol Hydrochloride Salt A mixture of 4-cyanophenol (Aldrich, 1 g, 8.40 mmol), K$_2$CO$_3$ (3.5 g, 25 mmol), and 2R-(–)-glycidyl-3-nitrobenzenesulfonate (2.18 g, 8.4 mmol) in acetone (25 mL) was refluxed for 16 h. The mixture was cooled, concentrated, taken up in H$_2$O and extracted with diethyl ether. The organic extracts were washed with saturated NaHCO$_3$, brine, dried over MgSO$_4$, filtered, and concentrated. This compound (0.260 g, 1.5 mmol) and 4-methoxyphenyl-1,1-dimethyl ethylamine (0.269 g, 1.5 mmol) in ethanol (10 mL) was heated at reflux for 16 h. The mixture was cooled, concentrated and purified by flash column chromatography (5% MeOH/CHCl$_3$) to afford an oil which was stirred in methanol and added 4M HCl, concentrated and triturated in ether to give the title compound as a white powder (0.060 g). ESMS (M+H)$^+$ m/e 355.1.

EXAMPLE 14

Preparation of (R)-1-[1,1-dimethyl-2-(4-methoxyphenyl)ethylamino]-3-[(4-methoxycarbonylmethyl)phenoxy]-propan-2-ol Hydrochloride Salt A mixture of methyl-4-hydroxyphenylacetate (Aldrich, 0.500 g, 2.99 mmol), K$_2$CO$_3$ (1.24 g, 8.89 mmol), and 2R-(−)-glycidyl-3-nitrobenzenesulfonate (0.777 g, 2.99 mmol) in acetone (10 mL) was refluxed for 16 h. The mixture was cooled, concentrated, taken up in H$_2$O and extracted with diethyl ether. The organic extracts were washed with 5% NaHCO$_3$, brine, dried over MgSO$_4$, filtered, and concentrated. This compound (0.200 g, 1.12 mmol) and 4-methoxyphenyl-1,1-dimethyl ethylamine (0.250 g, 1.12 mmol) in ethanol (10 mL) was heated at reflux for 16 h. The mixture was cooled, concentrated and purified by flash column chromatography (5% MeOH/CHCl$_3$) to afford an oil (0.266 g) of which 80 mg was stirred in methanol and added 4M HCl, concentrated and triturated in ether to give the title compound (0.060 g) with minor impurity of ethyl ester. ESMS (M+H)$^+$ m/e 402.2 & 416.4.

EXAMPLE 15

Preparation of (R)-1-[1,1-Dimethyl-2-(4-methoxyphenylethylamino]-3-[(2-nitro-4-cyano)phenoxy]-propan-2-ol Hydrochloride Salt A mixture of 4-hydroxy-3-nitrobenzonitrile (Aldrich, 0.500 g, 3.05 mmol), K$_2$CO$_3$ (1.26 g, 9.15 mmol), and 2R-(−)-glycidyl-3-nitrobenzenesulfonate (0.790 g, 3.05 mmol) in acetone (10 mL) was refluxed for 16 h. The mixture was cooled, concentrated, taken up in H$_2$O and extracted with diethyl ether. The organic extracts were washed with 5% NaHCO$_3$, brine, dried over MgSO$_4$, filtered. and concentrated. This compound (0.100 g, 0.45 mmol) and 4-methoxyphenyl-1,1-dimethyl ethylamine (0.085 g, 0.45 mmol) in ethanol (10 mL) was heated at reflux for 16 h. The mixture was cooled, concentrated and purified by flash column chromatography (5% MeOH/CHCl$_3$) to afford an oil which was stirred in methanol and added 4M HCl, concentrated and triturated in ether to give the title compound (0.030 g). ESMS (M+H)$^+$ m/e 400.1.

EXAMPLE 16

Preparation of (R)-1-[1,1-Dimethyl-2-(4-methoxyphenyl)ethylamino]-3-[(2-nitro-4-(hydroxymethyl))phenoxy]-propan-2-ol Hydrochloride Salt A mixture of 4-hydroxy-3-nitrobenzyl alcohol (Aldrich, 0.500 g, 2.96 mmol), K$_2$CO$_3$ (1.22 g, 8.87 mmol) and 2R-(−)-glycidyl-3-nitrobenzenesulfonate (0.767 g, 2.96 mmol) in acetone (10 mL) was refluxed for 16 h. The mixture was cooled, concentrated, taken up in H$_2$O and extracted with diethyl ether. The organic extracts were washed with 5% NaHCO$_3$, brine, dried over MgSO$_4$, filtered, and concentrated. This compound (0.252 g, 1.12 mmol) and 4-methoxyphenyl-1,1-dimethyl ethylamine (0.200 g, 1.12 mmol) in ethanol (10 mL) was heated at reflux for 16 h. The mixture was cooled, concentrated and purified by flash column chromatography (5% MeOH/CHCl$_3$) to afford an oil which was stirred in methanol and added 4M HCl, concentrated and triturated in ether to give the title compound (0.250 g). ESMS (M+H)$^+$ m/e 405.1.

EXAMPLE 17

Preparation of (R)-1-[1,1-Dimethyl-2-(4-methoxyphenyl)ethylamino]-3-[(2-nitro-4-methoxycarbonylmethyl)phenoxy]-propan-2-ol Hydrochloride Salt a) (R)-Methyl 4-(oxiranylmethoxy)-3-nitrophenylacetate The material purchased from Aldrich, 4-hydroxy-3-nitrophenyl acetic acid, (0.500 g, 2.54 mmol) was dissolved in methanol (5 mL) and was treated with concentrated H$_2$SO$_4$ (0.25 mL) at reflux for 16 h. The mixture was cooled, evaporated, taken up in 5% NaHCO$_3$ and extracted into ethyl ether. A mixture of this crude compound (0.512 g, 2.43 mmol), K$_2$CO$_3$ (1.0 g, 7.27 mmol) and 2R-(−)-glycidyl-3-nitrobenzenesulfonate (0.630 g, 2.43 mmol) in acetone (10 mL) was refluxed for 24 h. The mixture was cooled, concentrated and purified by flash column chromatography (50% EtOAc/Hexane) to afford the title compound (0.59 g) as an off-white foam. $^1$H-NMR (250 MHz, CDCl3): δ 2.84–2.93 (m, 2H), 3.37–3.450(m, 1H), 3.62 (s, 2H), 3.71 (s, 3H), 4.09–4.16 (m, 1H), 4.37–4.42 (m, 1H), 7.1–7.8 (m, 3H).

b) (R)-1-[1,1-Dimethyl-2-(4-methoxyphenyl)ethylamino]-3-[(2-nitro-4-methoxycarbonylmethyl)phenoxy]-propan-2-ol Hydrochloride Salt A mixture of the compound from Example 17 (a) (0.298 g, 1.12 mmol), and 4-methoxyphenyl-1,1-dimethyl ethylamine (0.200 g, 1.12 mmol) in ethanol (10 mL) was heated at reflux for 16 h. The mixture was cooled, concentrated and purified by flash column chromatography (5% MeOH/CHCl$_3$) to afford an oil (0.345 g) of which (0.110 g) was stirred in methanol and added 4M HCl, concentrated and triturated in ether to give a white powder of the title compound (0.067 g) with minor impurity of ethyl ester. ESMS (M+H)$^+$ m/e 447.2 & 461.2.

EXAMPLE 18

Preparation of (R)-1-[1,1-Dimethyl-2-(4-methoxyphenyl)ethylamino]-3-[(2-nitro-4-carboxymethyl)phenoxy]-propan-2-ol Hydrochloride Salt A mixture of the compound of Example 17(b)( 0.23 g, 0.51 mmol), and 1M NaOH (1.2 mL), was dissolved in methanol (5 mL) and stirred at rt for 24 h. The reaction was quenched with 1M HCl, extracted with CHCl$_3$, dried with MgSO$_4$, filtered and evaporated to afford the title compound as a white powder (0.060 g). ESMS (M+H)$^+$ m/e 433.2.

EXAMPLE 19

Preparation of (R)-1-[1,1-Dimethyl-2-(2-nanhthyl)ethylamino]-3-[(4-methoxycarbonylphenoxy]-propan-2-ol Hydrochloride Salt (a) Methyl 4-(R)-Glycidylbenzoate Methyl 4-hydroxybenzoate (1.0 g, 6.57 mmol, Aldrich) in acetone was treated with K$_2$CO$_3$ (2.72 g, 19.71 mmol) and 2R-(−)-glycidyl-3-nitrobenzenesulfonate (1.7 g, 6.57 mmol) and the solution heated at reflux for 24 h. The reaction mixture was filtered and the filtrate evalorated at reduced pressure. The residue was washed with 5% Na$_2$CO$_3$ (aqueous), dried over anhydrous $MgSO_4$ and evaporated to give methyl 4-(R)-glycidylbenzoate which was used without further purifcation in the next step.

(b) (R)-1-[1,1-Dimethyl-2-(2-naphthyl)ethylamino]-3-[(4-methoxycarbonyl)phenoxy]-propan-2-ol Hdrochloride Salt The epoxide from Example 19(a) (380 mg, 1.82 mmol) was treated with 1,1-dimethyl-2-(2-napthyl)ethylamine (364 mg, 1.82 mmol) in ethanol was heated at reflux for 24 h. The reaction mixture was evaporated and the residue purified by flash chromatography (silica gel, 3% MeOH in $CHCl_3$) to give the above titled product (344 mg). ES MS $(M+H)^+$ m/e 408.

EXAMPLE 20

Preparation of (R)-1-[1,1-Dimethyl-2-(2-naphthyl) ethylamino]-3-[(4-carboxy)phenoxy]-propan-2-ol Hydrochloride Salt The ester from Example 19(b) (281 mg, 0.69 mmol) in dioxane (4 mL) was treated with 1.4 mL of 1N NaOH (aqueous) at room temperature for 190 h. The reaction mixture was acidified with 3 N HCl (aqueous) and evaporated. The residue was washed with water and then azeotroped from $CH_2Cl_2$ to give the above titled compound (194 mg). ES MS $(M+H)^+$ m/e 394.

EXAMPLE 21

Preparation of (R)-1-[1,1-Dimethyl-2-(4-methoxyphenyl)ethylamino]-3-[(2-cyano-4-ethoxycarbonylmethyl)phenoxy]-propan-2-ol (a) Ethyl(2-Cyano-4-oxyacetyl)phenylacetate A solution of ethyl-4-hydroxyphenylacetate (2.34 g, 13 mmol), $SnCl_4$ (0.15 mL, 1.3 mmol) and tributylamine (1.2 mL, 5.2 mmol) in toluene (100 mL) was stirred at RT for 20 min under an argon atmosphere. Paraformaldehyde (0.86 g) was added and the solution was heated at reflux for 18 h. The solution was cooled to RT and poured into water and acidified with aqueous HCl (3M) to pH 2 (litmus paper). Ethylacetate was added and the layers separated. The organic layer was washed with water and brine and concentrated to an oil which was used without purification in the next step.

The above oil, hydroxylamine hydrochloride (0.69g, 10 mmol) and diisopropylethylamine (1.3 g, 10 mmole) in EtOH (20 mL) were heated at reflux under an argon atmosphere. After 18 h the solution was concentrated to give 2.1 g of an oil which was used in the next step without further purification.

A solution of the above oil in acetic anhydride (30 mL) was heated at reflux for 30 min. The solution was then concentrated. Flash chromatography (silica gel, 30% EtOAc/Hexane) yielded 0.7 g (22%) of the title compound. $^1$H-NMR (400 MHz, $CDCl_3$) δ 1.2–1.3 (m, 3H), 2.4 (s, 3H), 3.6 (s, 2H), 4.1–4.2 (q, 2H), 7.1–7.8 (m, 3H).

(b) (2R)-Glycidyl-[ethyl-2-cyano-4-hydroxyphenyl]acetate

A solution of ethyl-(2-cyano-4-hydroxyphenyl)acetate (0.5 g, 2 mmol) in EtOH/water (1:1, 10 mL) was treated with $K_2CO_3$ (0.28 g, 2 mmol). After 3 h the solution was concentrated. The residue was partitioned between EtOAc/water and aqueous HCl (1M) was added to adjust the solution to pH 2 (litmus paper). The EtOAc layer was separated and washed with water and concentrated to give 0.42 g of an oil.

A solution of the above oil (0.42 g, 2 mmol), (2R)-gycidyl 3-nitrobenzenesulfonate (Aldrich Chemicals, 0.52 g, 2 mmol) and $K_2CO_3$ (0.28 g, 2 mmol) in acetone (20 mL) was heated at reflux for 18 h. The solution was cooled and filtered. The filtrate was concentrated to an oil. Flash chromatography (silica gel, 20% EtOAc/Hexane) yielded 0.4 g (77%)of the title compound. $^1$H-NMR (400 MHz, $CDCl_3$) δ 1.2–1.3 (m, 3H), 2.7 (m, 1H), 2.8 (m, 1H), 3.4 (m, 1H), 3.6 (s, 2H), 4.0–4.2 (m, 3H), 4.4 (m, 1H), 7.0–7.5 (m, 3H).

(c) (R)-1-[1,1-Dimethyl-2-(4-methoxyphenyl)ethylamino]-3-[(2-cyano-4-ethoxycarbonylmethyl)phenoxy]-propan-2-ol A mixture of (2R)-glycidyl-(ethyl-2-cyano-4-hydroxyphenyl)acetate 0.2 g, 0.77 mmol), and 4-methoxyphenyl-1,1-dimethylethylamine (0.138 g, 0.77 mmol) in ethanol (20 mL) was heated at reflux for 24 h. The mixture was cooled, concentrated and purified by flash column chromatography on silica gel (5% MeOH/$CH_2Cl_2$) to afford the title compound as a colorless oil (0.207 g, 61%). ES MS $(M+H)^+$ m/e 441.2.

EXAMPLE 22

Preparation of (R)-1-[1,1-Dimethyl-2-(4-methoxyphenyl)ethylamino]-3-[(2-cyano-4-carboxymethyl)phenoxy]-propan-2-ol The compound of Example 21 (0.100 g, 0.23 mmol) was dissolved in methanol (10 mL) and was stirred with 1M NaOH aq (3 mL) at RT for 18 h. The reaction was concentrated in vacuo. The residue was treated with 2 ml of water and the pH adjusted to 5 with 1M HCl. The resulting gum was removed and concentrated twice from EtOH. Trituration with ether afforded a white powder (0.08 g, 84%). ES MS $(M+H)^+$ m/e 413.2

EXAMPLE 23

Preparation of (R)-1-[1,1-Dimethyl-2-(4-methoxyphenyl)ethylamino]-3-[(4-methoxycarbonylethyl)phenoxy]-propan-2-ol (a) (R)-Glycidyl-methyl-3-(4-hydroxyphenyl)propionate A solution of methyl-3-(4-hydroxyphenyl)propionate (Aldrich Chemicals, 1.8 g, 10 mmole), (R)-gycidol (Aldrich Chemicals 0.74 g, 10 mmol), triphenylphosphine (2.62 g, 10 mmole) and diisopropyl azodicarboxylate (2.02 g, 10 mmole) in 50 ml THF was stirred at RT for 18 h. The solution was filtered and the filtrate concentrated in vacuo. Flash chromatography (silica gel, $CH_2Cl_2$) afforded 1.33 g (56%)of the title compound. $^1$H-NMR (400 MHz, $CDCl_3$) δ 2.6 (m, 2H), 2.7 (m, 1H), 2.9 (m. 3H), 3.4 (m, 1H), 3.6 (s, 3H), 3.9 (m, 1H), 4.2 (m, 1H), 6.8–7.2 (m, 4H).

(b) (R)-1-[1,1-Dimethyl-2-(4-methoxyphenyl)ethylamino]-3-[(4-methoxycarbonylethyl)phenoxy]-propan-2-ol A mixture of (2R)-glycidyl-(ethyl-4-hydroxyphenyl) acetate (0.2 g, 0.85 mmol), and 4-methoxyphenyl-1,1-dimethylethylamine (0.15 g, 0.85 mmol) in ethanol (20 mL) was heated at reflux for 24 h. The mixture was cooled, concentrated and purified by flash column chromatography on silica gel (5% MeOH/$CH_2Cl_2$) to afford the title compound as a colorless oil (0.178 g, 51%). ESMS $(M+H)^+$ m/e 416.3. afforded a white powder (0.081 g, 70%). ESMS $(M+H)^+$ m/e 402.3

EXAMPLE 24

Preparation of N-[2R-Hydroxy-3-[[2-nitro-4-[2S-ethoxycarbonyl-2-[methylsulfonyl]amino]phenoxy] propyl]-1,1-dimethyl-2-[4-methoxyphenyl] ethylamine Hydrochloride (a) Methyl-2S-amino-3-[[3-nitro-4-hydroxy]phenyl] propionate A solution of 3-nitro-L-tyrosine (25 g, 110.54 mmole) in methanol (250 mL, pre-saturated with HCl gas) was heated at reflux for 16 h. The mixture was cooled, concentrated, taken up in $H_2O$, neutralized with $K_2CO_3$(s), filtered the orange solid, washed with H₂O. dried by air (22 g, 83%). ¹H-NMR (400 MHz, DMSO-d₆) δ 2.75 (dd, J=7.6, 13.6 Hz, 1H), 2.84 (dd, J=76, 13.6 Hz, 1H), 3.55 (m, 1H), 3.60 (s, 3H), 7.04 (d, J=8.5 Hz, 1H), 7.35 (d, J=8.5 Hz, 1H), 7.71 (s, 1H).

(b) Methyl-2S-[methylsulfonyl]amino-3-[[3-nitro-4-hydroxy]phenyl]propionate

To a stirred mixture of Example 24(a) (1 g, 4.16 mmole), and pyridine (0.33 g, 4.16 mmole) in dried THF (30 mL) was added methanesulfonylchloride (0.48 g, 4.16 mmole). After stirring at RT overnight, the mixture was concentrated, taken up in H₂O, extracted with EtOAc, washed with 5% HCl, saturated NaHCO₃, brine, dried over MgSO₄, concentrated to give a light brown oil (0.98 g, 74%). ¹H-NMR (400 MHz, DMSO-d₆): δ 2.70 (s, 3H), 2.85 (dd, J=1 1.2, 14.1 Hz, 1H), 3.05 (dd, 4.9, 11.2 Hz, 1H), 3.67 (s, 3H), 4.20 (m, 1H), 7.07 (d, J=8.5 Hz, 1H), 7.47 (dd, J=1.8, 8.5 Hz, 1H), 7.82 (d, J=1.8 Hz, 1H), 7.9 (d, J=8.5 Hz, 1H).

(c) Methyl-2S-[metbylsulfonyl]amino-3-[[3-nitro-4-R-glycidyl]phenyl]propionate

A mixture of Example 24(b) (0.98 g, 3.08 mmole), K₂CO₃ (0.85 g, 6.16 mmole), and 2R-glycidyl-3-nitrobenzenesulfonate (0.83 g, 3.23 mmole) in acetone (20 mL) was heated at reflux in 24 h. The mixture was concentrated, taken up in H₂O, extratcted with EtOAc. The organic extracts were washed with brine, dried over MgSO₄, concentrated, purified by flash column chromatography (50% EtOAc/Hexane) to afford a light yellow oil (0.4 g, 35%). ¹H-NMR (400 MHz, CDCl₃) δ 2.70 (s, 3H), 2.82 (dd, J=4.9, 11.2 Hz, 1H), 2.88 (dd, J=4.9, 11.2 Hz, 1H), 3.32 (m, 1H), 3.51 (dd, J=11.2, 14.1 Hz, 1H), 3.55 (dd, 4.9, 11.2 Hz, 1H), 3.7 (s, 3H), 4.10 (dd, J=4.9, 11.2 Hz, 1H), 4.33 (dd, J=2.2, 4.9 Hz, 1H), 5.10 (dd, J+4.9, 11.2 Hz, 1H), 6.97 (dd, J=1.8, 8.5 Hz, 1H), 7.36 (dd, J=1.8, 8.5, 1H), 7.64 (s, 1H).

(d) N-[2R-Hydroxy-3-[[2-nitro-4-[2S-ethoxycarbonyl-2-[methylsulfonyl]amino]phenoxy]propyl]-1,1-dimethyl-2-[4-methoxyphenyl]ethylamine Hydrochloride A mixture of Example 24(c) (0.22 g, 0.59 mmole), LiClO₄, and 1,1-dimethyl-2-[4-methoxyphenyl]ethylamine (0.13 g, 0.7102 mmole) in EtOH (5 mL) was heated at reflux in 24 h. The mixture was cooled, concentrated, taken up in H₂O, extracted with EtOAc. The organic extracts were dried over MgSO₄, concentrated, and purified by flash column chromatography (3% MeOH/CH₂Cl₂) to afford a yellow oil, which was dissolved in THF and added 4M Hcl in p-dioxane, concentrated, and co-evaporated with ether to give an off white foam (0.26 g, 79%). ¹H-NMR (400 MHz, CDCl₃) δ 1.17 (s, 6H), 2.63 (s, 1H), 2.77 (s, 2H), 2.87 (dd, J=4.9, 11.2 Hz, 1H), 3.07 (m, 3H), 3.17 (dd, J=4.9, 11.2 Hz, 1H), 3.69 (m, 1H), 3.70 (s, 3H), 4.14 (s, 3H), 4.37 (t, J–7.2 Hz, 1H), 6.81 (dd, J=1.8, 8.5 Hz, 1H), 7.10 (m, 3H), 7.45 (dd, J=1.8, 8.5 Hz, 1H), 7.72 (s, 1H).

EXAMPLE 25

Preparation of N-[2R-hydroxy-3-[[2-nitro-4-[2S-methoxycarbonyl-2-[phthalimido]phenoxy]propyl]1,1-dimethyl-2-[naphthyl]ethylamine Hydrochloride (a) Methyl-2S-[phthalimido]-3-[[3-nitro-4-hydroxy]phenyl] propionate A mixture of Example 24(a) (5 g, 20.82 mmole), and phthalic anhydride (3.4 g, 22.9 mmole) in CHCl₃ (150 mL) was heated at reflux in 24h. To the mixture was added Et₃N (10.6 g, 104.08 mmole), and cooled, concentrated, taken up in H₂O, extracted with EtOAc. The organic extracts were washed with 6N HCl, saturated Na₂HCO₃, brine, dried over MgSO₄, concentrated to afford a yellow oil (7 g, 91%). ¹H-NMR (400 MHz, DMSO-d₆) δ 3.24 (dd, J=11.2, 14.1 Hz, 1H), 3.45 (dd, J=4.9, 11.2 Hz, 1H), 3.70 (s, 3H), 5.28 (dd, J=4.9, 11.2 Hz, 1H), 6.95 (d, 8.3 Hz, 1H), 7.34 (dd, J=2.3, 8.3 Hz, 1H), 7.70 (d, J=2.3 Hz, 1H), 7.87 (m, 4H).

(b) Methyl-2S-[phthalimido]-3-[[3-nitro-4-R-glycidyl] phenyl]propionate

Following the example 24(c), the title compound was prepared as a tan solid (7.9 g, 98%). ¹H-NMR (400 MHz, CDCl₃) δ 2.82 (dd, J=4.9, 111.2 Hz, 1H), 2.88 (dd, J=4.9, 11.2 Hz, 1H), 3.32 (m, 1H), 3.51 (dd, J=11.2, 14.1 Hz, 1H), 3.55 (dd, J=4.9, 11.2Hz, 1H), 3.7 (s, 3H), 4.10 (dd, J=4.9, 11.2Hz, 1H), 4.33 (dd, J=2.2, 4.9 Hz, 1H), 5.10 (dd, J=4.9, 11.2 Hz, 1H), 6.97 (dd, J=1.8, 8.5 Hz, 1H), 7.36 (dd, J=1.8, 8.5 Hz, 1H), 7.64 (s, 1H), 7.73 (m, 2H), 7.81 (m, 2H).

(c) N-[2R-Hydroxy-3-[[2-nitro-4-[2S-methoxycarbonyl-2-[phthalimido]phenoxy]propyl]-1,1-dimethyl-2-[naphthyl]ethylamine Hydrochloride A mixture of Example 25(b) (1 g, 2.35 mmole), LiClO₄ 0.65 g, 4.69 mmole), and 1,1-dimethyl-2-naphthylamine (0.47 g, 2.35 mmole) in MeCN (20 mL) was heated at reflux in 24h. The mixture was cooled, concentrated, taken up in H₂O, extracted with EtOAc. The organic extracts were washed with brine, dried over MgSO₄, concentrated and purified by flash column chromatography (3% MeOH/CH₂Cl₂) to afford a light yellow foam, which was dissolved in ether and added 4M HCl in p-dioxane, concentrated, and co-evaporated with ether/hexane to give an off white solid (1.08 g, 74%). ¹H-NMR (400 MHz, CDCl₃) δ 1.35 (s, 6H), 3.10 (s, 2H), 3.3 (m, 2H), 3.53 (m, 2H), 3.78 (s, 3H), 3.98 (m, 1H), 4.14 (m, 1H), 4.37 (m, 1H), 5.06 (m, 1H), 6.91 (d, J=8.5 Hz, 1H), 7.30 (m, 2H), 7.41 (m, 2H), 7.79 (m, 9H).

EXAMPLE 26

Preparation of N-[2R-Hydroxy-3-[[2-nitro-4-[2S-carboxy-2-[[[2-carboxylphenyl]carbonyl]amino] ethyl]phenoxy]propyl]-1,1-dimethyl-2-[naphthyl] ethylamine (a) N-[2R-Hydroxy-3-[[2-nitro-4-[2S-carboxy-2-[[[2-carboxy]phenyl]carbonyl]amino]ethyl]phenoxy]propyl]-1,1-dimethyl-2-[naphthyl]ethylamine A mixture of Example 25(c) (0.20 g, 0.32 mmole), and LiOH.H₂O (0.03 g, 0.64 mmole) in THF/H₂0 (5 mL, 4:1) was stirred at RT in 24 h. The mixture was concentrated, taken up in H₂O, acidified with AcOH, filtered the solid, triturated in ether to give an off white solid (0.15 g, 71%). ¹H-NMR (400 MHz, DMSO-d₆) δ 1.25 (s, 6H), 3.05 (m, 2H), 3.15 (s, 2H), 3.25 (m, 2H), 4.21 (m, 3H), 4.61 (m, 1H), 7.45 (m, 7H), 7.82 (m, 7H), 8.83 (d, J=4.9 Hz, 1H).

EXAMPLE 27

Preparation of N-[2R-Hydroxy-3-[[2-nitro-4-[2S-methoxycarbonyl-2-[[[2-carboxy]phenyl]carbonyl] amino]ethyl]phenoxy]propyl]-1,1-dimethyl-2-[naphthyl]ethylamine Hydrochloride (a) N-[2R-Hydroxy-3-[[2-nitro-4-[2S-methoxycarbonyl-2-[[[2-carboxy]phenyl]carbonyl]amino]ethyl]phenoxy] propyl]-1,1-dimethyl-2-[naphthyl]ethylamine Hydrochloride A mixture of Example 25(c) (0.20 g, 0.32 mmole), and LiOH.H₂O (0.02 g, 0.32 mmole) in THF/H₂O (5 mL, 4:1) was stirred at RT in 24 h. The mixture was concentrated, taken up in H₂O, acidified with AcOH, filtered the solid, triturated in ether to give an off white solid (0.10 g, 50%). ¹H NMR (400 MHz, DMSO-d₆) δ 1.25 (s, 6H), 3.05 (m, 2H), 3.15 (s, 2H), 3.25 (m, 2H), 3.78 (s, 3H), 4.21 (m, 3H), 4.61 (m, 1H), 7.45 (m, 7H), 7.82 (m, 7H), 8.83 (d, J=4.9 Hz, 1H). ¹H-NMR (400 MHz, DMSO-d₆): δ 1.25 (s, 6H), 3.05

(m, 2H), 3.15 (s, 2H), 3.25 (m, 2H), 4.21 (m, 3H), 4.61 (m, 1H), 7.45 (m, 7H), 7.82 (m, 7H), 8.83 (d, J=4.9 Hz, 1H).

EXAMPLE 28

Preparation of (R)-1-1,1-Dimethyl-2-(2-naphthyl)ethylamino]-3-[(3-(2-aminophenoxy)-4-methoxycarbonyl)phenoxy]-propan-2-ol Dihydrochloride Salt (a) 1-(2-Nitrophenoxy)-2-methoxycarbonyl-5-methoxybenzene A solution of 2-methoxycarbonyl-5-methoxyphenol (34.1 g, 0.187 mol), 2-nitrofluorobenzene (19.7 mL, 0.187 mol), and $K_2CO_3$ (65 g, 0.467 mol) in DMF (200 mL) was heated at 110° C. for 18 h. The solution was diluted with water (200 mL) and extracted with EtOAc. The EtOAc layer was concentrated to give the crude title compound (57 g)which was used as is for the next step without further purification.

(b) 2-Carboxymethyl-5-methoxy-phenyl-oxy-(3-aminobenzene)

A solution of compound from Example 28(a) (57 g, 0.187 mol) and 10% Pd/C (11 g) in MeOH (1000 mL) was treated with $H_2$ at 50 psi for 2 h. The solution was filtered through Celite and the filtrate was concentrated. Flash chromatography (silica gel, 20% EtOAc/Hexane) yielded the title compound (49.3 g, 96%): MS (ES) $(M+H)^+$ m/e 274.1.

(c) 1-(2-Aminophenoxy)-2-methoxycarbonyl-5-hydroxybenzene

To a cold solution of compound from Example 28(b) (1 g, 4.1 mmol) and ethylmercaptan (1.5 mL, 20 mmol) in $CH_2Cl_2$ (15 mL) was added $AlCl_3$ (2.8 g, 20 mmol). After 2 h at 0° C. solution was concentrated and residue was treated with ice/water (50 mL) and $CH_2Cl_2$ (50 mL). Organic layer was separated and washed with water (2×). The organic layer was concentrated to give the crude title compound (0.95 g) which was used as is for the next step.

(d) 1-(2-Aminophenoxy)-2-methoxycarbonyl-5-(2(R)-glycidyl)-benzene

A solution of compound from Example 28(c) (0.51 g 2.2 mmol), 2R-gycidyl 3-nitrobenzenesulfonate (0.582 g, 2.2 mmol) and $K_2CO_3$ (0.93 g, 6.6 mmol) in acetone (20 mL) was heated at reflux for 18 h. The solution was filtered and the filtrate was concentrated to give the title compound (0.64 g) which was used as is for the next step.

(e) (R)-1-[1,1-Dimethyl-2-(2-naphthyl)ethylamino]-3-[(3-(2-aminophenoxy)-4-methoxycarbonyl)phenoxy]-propan-2-ol dihydrochloride salt A solution of compound from Example 28(d) (0.10 g, 0.4 mmol) and 1,1-dimethyl-2-(2-naphthyl)ethyl amine (0.07 g, 0.4 mmol) in EtOH (5 mL) was heated to reflux for 18 hr. Solution was concentrated. Flash chromatography (silica gel, 5% $CH_3OH/CH_2Cl_2$) and treatment with HCl in MeOH yielded the title compound (0.1 g, 60%): $^1$H-NMR (400 MHz, DMSO-$d_6$) δ 1.0–1.3 (m,8H), 3.0–4.3 (m, 11H), 6.7–8.0 (m, 11H), 8.8–8.9 (m, 1H), 9.3–9.4 (m, 1H); MS (ES) $(M+H)^+$ m/e 515.0.

EXAMPLE 29

Preparation of (R)-1-1,1-Dimethyl-2-(2-naphthyl)ethylamino]-3-[(3-(2-aminophenoxy)-4-carboxy)phenoxy]-propan-2-ol Dihydrochloride Salt A solution of compound from Example 28(e) (0.7 g, 1.4 mmol) in MeOH (5 mL) was treated with 1 N NaOH (3.0 mL, 3.0 mmol). After 18 h, the solution was concentrated. Water (10 mL) was added and the solution was treated with 1 N HCl to pH 7, filtered and the solid was dried in vacuo to give the title compound (0.35 g, 50%). MS (ES) $(M+H)^+$ m/e 501.1; $^1$H-NMR (400 MHz, DMSO-$d_6$) δ 1.2–1.3 (s, 6H), 3.1–4.3 (m, 11H), 6.7–7.9 (m, 13H), 8.7–8.9 (m, 1H), 9.2–9.5 (m, 1H).

Formulations for pharmaceutical use incorporating compounds of the present invention can be prepared in various forms and with numerous excipients. Examples of such formulations are given below.

EXAMPLE 30

Preparation of (R)-N-[2-Hydroxy-3-(2-cyano-4-(2-carboethoxyethyl)phenoxy)propylyl]-1,1-dimethyl-2-(2-naphthyl)ethylamine (a) Ethyl-3-(2-cyano-4-hydroxyphenyl)propionate To 25.2 g (0.13 mol) of ethyl-3-(4-hydroxy-3-cyanophenyl)propionate in 300 mL of dry toluene was added under argon 12.4 mL (0.052 mol) of tri-n-butylamine followed by 1.5 mL (0.013 mol) of tin(IV) chloride. After stirring for 10 min, 8.6 g of paraformaldehyde was added and the reaction was refluxed under argon for 18 h.

The reaction was cooled and concentrated to a dark oil which was subjected to flash column chromatography on silica gel eluting with 90:10 hexane:ethyl acetate (v/v). There was obtained 5.3 g of product (18.6%). Further elution with 70:30 hexane:ethyl acetate (v/v) yielded 12 g of starting material.

To a solution of 10 g (0.045 mol) of the above aldehyde in 200 mL of absolute ethanol was added 6.1 (0.06 mol) of triethylamine followed by 3.48 g (0.05 mol) of hydroxylamine hydrochloride. The reaction was stirred under argon at reflux for 18 h. The reaction was concentrated. The residual oil was dissolved in ethyl acetate and washed with IN HCl. The ethyl acetate phase was dried, filtered and concentrated to an oil which was treated with 100 mL of acetic anhydride and refluxed under argon for 30 min. The reaction was concentrated. The resulting oil was dissolved in ethyl acetate and washed with water. The ethyl acetate layer was dried, filtered and concentrated to an oil which was dissolved in 200 mL of ethanol and treated with a solution of 9.54 g of sodium carbonate (0.09 mol) in 50 mL of water. After stirring at room temperature for 5 h the mixture was neutralized with 3N HCl to pH 5 and concentrated. The resulting mixture was extracted with ethyl acetate. The ethyl acetate solution was dried, filtered and concentrated to an oil which solidified on storage: 9.5 g (97%).

(b) Ethyl-3-(2-cyano-4-(R)-glycidyloxyphenyl)propionate

A solution of 7.7 g (0.035 mol) ethyl-3-(2-cyano-4-hydroxyphenyl)propionate and 9.1 g (0.035 mol) of 2-(R)-glycidyl-3-nitrobenzenesulfonate in 100 mL of dry acetone was treated with 7.6 g (0.055 mol) of potassium carbonate and refluxed under argon for 18 h. The reaction was cooled and filtered. The filtrate was concentrated and purified by flash column chromatography on silica gel eluting with 70:30 hexane:ethyl acetate to yield 6 g (62%) of the epoxide.

(c) (R)-N-[2-Hydroxy-3-(2-cyano-4-(3-carboethoxyethyl)phenoxy)propyl]-1,1-dimethyl-2-(2-naphthyl)ethylamine A solution of 2.69 g (0.0098 mol) of the epoxide and 1.95 g of the amine(0.098 mol) was refluxed in 75 mL of ethanol under argon for 18 h. The reaction was concentrated and the residue was purified by flash column chromatography on silica gel eluting with 95:5 methylene chloride:methanol (v:v) to yield 4.0 g of the desired product (86%).

EXAMPLE 31

Preparation of (R)-N-[2-Hydroxy-3-(2-cyano-4-(3-carboxyethyl)phenoxy)propyl]-1,1-dimethyl-2-(2-naphthyl)ethylamine Sodium Salt To a stirred solution of 100 mg of the ethyl ester(0.21 mmol) in 5 mL of ethanol was added 1 mL of 1N sodium hydroxide (1 mmol). The mixture was stirred for 4 h and then concentrated, diluted with 0.5 mL water and the pH adjusted to about 4 with 3N hydrochloric acid. The mixture was decanted and the residual gum was treated with 2 mL of 1N hydrochloric acid in methanol and concentrated. The residue was then concentrated four times from ethanol. The resulting solid was triturated with ether, filtered and dried under vacuum to give 60 mg of a white powder (64%), ES-MS, m/z 446.7 (M+H).

EXAMPLE 32

Preparation of (R)-N-[2-Hydroxy-3-(2-cyano-5-(3-carbethoxypropyl)phenoxy)propyl]-1,1-dimethyl-2-(2-naphthyl)ethylamine Hydrochloride (a) Ethyl 4-(4-cyano-3-hydroxyphenyl)butanoate To a solution of 2-fluoro-4-bromobenzonitrile (2.0 g, 10 mmol) in 10 mL of THF, cooled to −15° C., was added a solution of potassium t-butoxide (10 mL, 10 mmol) over 7 min. The cooling bath was removed, and the reaction stirred for another 40 min. The reaction was poured into ether/10% HCl, and the ether layer was separated. The ether layer was washed with water and saturated brine, dried over sodium sulfate, and concentrated to give 2.5 g of 2-t-butoxy-4-bromobenzonitrile.

Isobutyl vinylacetate (5.69 g, 40 mmol) was placed in a dry 500 mL flask, cooled to 0° C., and purged with $N_2$. A 0.5 M THF solution of 9-BBN (80 mL, 40 mmol) was added over 5 min with ice bath cooling. The bath was removed, and the reaction was stirred overnight at room temperature. To 2-t-butoxy-4-bromobenzonitrile (10.2 g, 40 mmol) was added 60 mL of dry DMF. The solution was placed under $N_2$, and $PdCl_2(dppf)$ (0.98 g, 1.2 mmol) was added over 1 min with vigorous stirring. The resulting solution was added by syringe to the above described borane solution, followed by the addition of $Cs_2CO_3$ (26.07 g, 80 mmol). The solution was heated to 90° C. for 45 min then allowed to cool. The reaction was worked up by pouring into ether/5% HCl. The ether layer was separated, and the aqueous layer was extracted once more with ether. The combined ether extracts were washed with water (3×1 L) and brine, dried over sodium sulfate and concentrated. The product, isobutyl 4-(4-cyano-3-t-butoxyphenyl)butanoate, was used as is for the next reaction.

All of the ester from above was dissolved in 125 mL of THF to which was added 50 mL of water containing 80 mmol of LiOH. The solution was heated to 65–72° C. for 5.5 hours, then concentrated in vacuo. The residue was taken up in ether/water and the ether layer separated. The aqueous layer was extracted twice more with ether to remove any non-acidic impurities. The aqueous layer was made acidic with HCl, and extracted twice with ether. The combined ether extracts were washed with brine, dried over sodium sulfate and concentrated to give 11.1 g of 4-(4-cyano-3-t-butoxyphenyl)butanoic acid (still containing some cyclooctyl impurities derived from the 9-BBN).

The above acid (approx. 40 mmol) was dissolved in dry THF and placed under $N_2$. 1,1'-Carbonyldiimidazole (6.81 g, 42 mmol) was added, and the reaction was stirred for 2 hrs at room temperature. Dry ethanol (5.552 g, 120 mmol), to which NaH (80 mg, 2 mmol) had been added, was then added to the solution and stirred at room temperature for 1 hr followed by heating to 50–60° C. for 3 hours. The solution was concentrated, and the residue taken up in ether/5% HCl. The ether layer was separated, washed with water, $NaHCO_3$ and brine, then dried over sodium sulfate and concentrated to give 9.3 g of crude product. The crude product was chromatographed on a silica gel column (5×20 cm) equilibrated in $CHCl_3$ and eluted with 4% EtOAc in $CHCl_3$. The yield of was 7.15 g (62% over 3 steps from 2-t-butoxy-4-bromobenzonitrile).

Ethyl 4-(4-cyano-3-t-butoxyphenyl)butanoate (6.8 g, 23.5 mmol) was dissolved in a mixture of acetonitrile (42 mL) and conc. HCl (3.85 mL) and allowed to stand for 80 min. The reaction was poured into ether/water and the ether layer separated. The ether layer was washed with water and brine, and the combined aqueous washes were reextracted once with ether. The combined ether layers were dried over sodium sulfate and concentrated to give 5.1 g of an off white waxy solid. This material was loaded onto a silica gel column (5×15 cm) in $CHCl_3$ and eluted with 20% EtOAc in $CHCl_3$ to yield 4.5 g of ethyl 4-(4-cyano-3-hydroxyphenyl) butanoate: $^1$H-NMR ($CDCl_3$) 8.2 (1H, s), 7.42 (1H, d), 6.95 (1H, s), 6.77 (1H, d), 4.2 (2H, q), 2.63 (2H, dd), 2.39 (2H, dd), 1.96 (2H, m), 1.28 (3H, t); $^{13}$C ($CDCl_3$) 174.4, 159.5, 149.2, 132.8, 120.8, 117.0, 116.1, 97.1, 60.9, 35.2, 33.6, 25.7. 14.1.

(b) Preparation of (R)-2-Cyano-5-(3-carbethoxypropyl) phenyl Glycidyl Ether

Using the method of example 30(b), vide supra, ethyl 4-(4-cyano-3-hydroxyphenyl)butanoate (1.4 g, 6 mmol) and (R)-glycidyl nosylate (1.48 g, 5.71 mmol) were used to prepare 1.47 g (88%) of the title compound as a white solid.

(c) (R)-N-[2-Hydroxy-3-(2-cyano-5-(3-carbethoxypropyl) phenoxy)propyl]-1,1-dimethyl-2-(2-naphthyl)ethylamine Hydrochloride.

Using the method of example 30(c), supra, (R)-2-cyano-5-(3-carbethoxypropyl)phenyl glycidyl ether (1.47 g, 5.08 mmol) and 1,1-dimethyl-2-(2-naphthyl)ethylamine (1.1 g, 5.59 mmol) were used to prepare the title compound as a white solid: $^1$H-NMR ($CDCl_3$) δ 9.82 (1H, br s), 8.42 (1H, br s), 7.78 (4H, m), 7.35–7.5 (4H), 6.8 (2H, m), 5.7 (1H, br s), 4.82 (1H, m), 4.25 (2H, m), 4.1 (2H, q), 3.4–3.65 (4H), 2.65 (2H, dd), 2.3 (2H,dd), 1.95 (2H, m), 1.55 (6H, d), 1.25 (3H, t): $^{13}$C-NMR ($CDCl_3$) 173.0, 160.1, 149.4, 133.2, 133.1, 132.4, 131.9, 129.7, 128.7, 128.0, 127.7, 127.5, 126.2, 125.9, 121.7, 116.5, 113.1, 99.8, 70.7, 65.6, 61.4, 60.4, 45.1, 44.2, 35.5, 33.4, 25.9, 23.1, 22.9, 14.2.

EXAMPLE 33

Preparation of (R)-N-[2-Hydroxy-3-(2-cyano-5-(3-carboxypropyl)phenoxy)propyl]-1,1-dimethyl-2-(2-naphthyl)ethylamine Sodium Salt (R)-N-[2-Hydroxy-3-(2-cyano-5-(3-carbethoxypropyl) phenoxy)propyl]-1,1-dimethyl-2-(2-naphthyl)ethylamine (0.77 g, 1.58 mmol) was hydrolyzed by stirring overnight at room temperature in 25 mL of EtOH containing 2.37 mmol of NaOH in 2.37 mL of water. The reaction was concentrated, and the residue dissolved in 40 mL of water. The pH was lowered with 1 N HCl until the zwitterion form of the product dropped out of solution (pH approx. 6 to 6.5). The solid was filtered and washed with water. The solid was then suspended in 30 mL of water, and 1 N NaOH was added slowly until the solid went into solution (final pH approx. 11). The solution was frozen and lyophilized to dryness to give 732 mg of the title compound as a white solid: $^1$H-NMR (1:1 $CD_3CN:D_2O$) 7.6–7.8 (4H), 7.4 (3H, m), 7.32 (1H, d), 7.0 (1H, s), 6.9 (1H, d), 4.1 (2H, m), 4.0 (1H, m), 3.78–3.92 (4H), 2.6 (2H, dd), 2.1 (2H, dd), 1.8 (2H, m), 1.02 (6H, d); $^{13}$C-NMR (1:1 $CD_3CN:D_2O$) 181.7, 160.8, 151.8, 136.4, 133.7, 133.5, 132.2, 129.6, 129.0, 127.7, 127.5, 126.3, 125.7, 121.9, 117.6, 113.3, 98.2, 71.4, 69.1, 53.7, 46.5, 44.5, 37.5, 36.0, 27.8, 26.1, 26.0.

EXAMPLE 34

Preparation of (R)-N-[2-Hydroxy-3-(2-cyano-5-(2-carbethoxyethyl)phenoxy)propyl]-1,1-dimethyl-2-(2-naphthyl)ethylamine Hydrochloride (a) Ethyl 3-(4-cyano-3-hydroxyphenyl)propionate Trifluoromethanesulfonic anhydride (9.0 mL, 15 g, 53 mmol, 1.2 equiv) was added over a period of 5 min to a solution of ethyl 3-(4-hydroxy-3-methoxyphenyl)propionate (8.7 mL, 10 g, 45 mmol, 1 equiv) and pyridine (9.0 mL, 8.8 g, 110 mmol, 2.5 equiv) in $CH_2Cl_2$ (40 mL) cooled to 0° C. in an ice bath. The ice bath was removed and the reaction mixture was stirred for 24 h. The reaction mixture was concentrated. This material was then taken up in $Et_2O$ (100 mL) and washed with 0.1 M HCl (2×50 mL). The organic layer was dried (anh. $Na_2SO_4$) and concentrated (75° C.). This yielded 13.7 g (86%) of product as a yellow oil. The crude material (13.3 g) was flash chromatographed (1000 mL 9:1 hex/EtOAc, 500 mL 4:1 hex/EtOAc) through flash silica gel (200 mm×50 mm dia.). The fractions containing only product were combined and concentrated (75° C.). This provided 12.3 g of ethyl 3-(4-trifluoromethanesulfoxy-3-methoxyphenyl)propionate as a nearly-colorless oil.

To a mixture of ethyl 3-(4-trifluoromethanesulfoxy-3-methoxyphenyl)propionate (11.9 g, 33.4 mmol, 1 equiv) and zinc cyanide (7.8 g, 66.4 mmol, 2.0 equiv) in deoxygenated dry DMF (60 mL) was added tetrakis(triphenylphosphine)palladium(0) (1.3 g, 1.1 mmol, 0.034 equiv). The reaction mixture was stirred at 120° C. for 5 h. The reaction mixture was then filtered through Celite®. The filtrate was diluted with satd aq $NaHCO_3$ (100 mL) and $H_2O$ (100 mL) and extracted with EtOAc (1×100 mL). The organic layer was then washed with $H_2O$ (2×50 mL), dried (anh. $Na_2SO_4$), and concentrated (75° C.). This gave 6.99 g (89.7%) of crude product as a brown oil. This oil was flash chromatographed (500 mL 9:1 hex/EtOAc, 1500 mL 3:1 hex/EtOAc) through flash silica gel (200 mm×50 mm dia.). The fraction containing product was concentrated (75° C.) yielding 4.70 g (60.3%) of ethyl 3-(4-cyano-3-methoxyphenyl)propionate as a white crystalline solid.

A mixture of ethyl 3-(4-cyano-3-methoxyphenyl) propionate (3.17 g, 13.6 mmol, 1 equiv) and sodium cyanide (2.00 g, 40.8 mmol, 3.00 equiv) in DMSO (60 mL) was stirred at 140–180° C. for 2 h. After 2.5 hours the reaction mixture was taken up in $H_2O$ (300 mL), adjusted to pH 7 with AcOH (2.1 mL), and extracted with $Et_2O$ (1×150 mL). The organic layer was washed with $H_2O$ (2×50 mL), dried (anh. $Na_2SO_4$), and concentrated (75° C.). This yielded 2.05 g (68.8%) of ethyl 4-(4-cyano-3-hydroxyphenyl)propionate as a light yellow crystalline solid: $^1$H-NMR ($CDCl_3$) 7.42 (1H, d), 7.40 (1H, br s), 6.92 (1H, d), 6.81 (1H, dd), 4.15 (2H, q), 2.94 (2H, dd), 2.64 (2H, dd), 1.25 (3H, t).

(b) (R)-2-cyano-5-(2-carbethoxyethyl)phenyl Glycidyl Ether

Using the method of example 30(b), supra, ethyl 3-(4-cyano-3-hydroxyphenyl)propionate (1.32 g, 6 mmol) and (R)-glycidyl nosylate (1.48 g, 5.71 mmol) were used to prepare 1.35 g (86%) of the title compound as a white solid.

(c) (R)-N-[2-Hydroxy-3-(2-cyano-5-(2-carbethoxyethyl)phenoxy)propyl-1,1-dimethyl-2-(2-naphthyl)ethylamine Hydrochloride Using the method of example 30(c), supra, (R)-2-cyano-5-(2-carbethoxyethyl)phenyl glycidyl ether (1.35 g, 4.9 mmol) and 1,1-dimethyl-2-(2-naphthyl)ethylamine (1.07 g, 5.39 mmol) were used to prepare the title compound as a white solid: $^1$H-NMR ($CDCl_3$) 9.82 (1H, br m), 8.45 (1H, br m), 7.7–7.8 (4H), 7.3–7.48 (4H), 6.82 (2H, m), 5.68 (1H, d), 4.82 (1H, br m), 4.25 (2H, m), 4.10 (2H, q), 3.38–3.62 (4H), 2.92 (2H, t), 2.60 (2H, t), 1.52 (6H, d), 1.22 (3H, t); $^{13}$C-NMR ($CDCl_3$) 172.12, 160.11, 148.42, 133.23, 133.18, 132.39, 131.93, 129.70, 128.73, 127.96, 127.70, 127.48, 126.16, 125.91, 121.57, 116.45, 113.07, 100.11, 70.73, 65.62, 61.46, 60.61, 45.06, 44.22, 34.96, 31.17, 23.12, 22.94, 14.14.

EXAMPLE 35

Preparation of (R)-N-[2-Hydroxy-3-(2-cyano-5-(2-carbethoxy)phenoxy)propyl]-1,1-dimethyl-2-(2-naphthyl)ethylamine Sodium Salt (R)-N-[2-Hydroxy-3-(2-cyano-5-(2-carbethoxyethyl)phenoxy)propyl]-1,1-dimethyl-2-(2-naphthyl)ethylamine (0.54 g, 1.14 mmol) was hydrolyzed by the method of example 34. supra, to give 510 mg of the title compound as a white solid: $^1$H-NMR (1:1 $CD_3CN:D_2O$) 7.6–7.8 (4H), 7.40 (3H, m), 7.34 (1H, d), 7.00 (1H, s), 6.90 (1H, d), 4.10 (2H, m), 4.00 (1H, m), 2.83 (6H, m), 2.39 (2H, dd), 1.02 (6H, d); $^{13}$C-NMR (1:1 $CD_3CN:D_2O$) 180.57, 160.77, 151.51, 136.47, 133.76, 133.55, 132.28, 129.68, 129.07, 127.78, 127.49, 126.32, 125.77, 121.76, 117.58, 113.18, 98.30, 71.48, 69.08, 53.71, 46.56, 44.59, 38.98, 33.10, 26.11, 25.92.

EXAMPLE 36

Preparation of (R)-N-[2-Hydroxy-3-(2-cyano-4-(3-carbethoxypropyl)phenoxy)propyl]-1,1-dimethyl-2-(2-naphthyl)ethylamine Hydrochloride (a) Ethyl 4-(3-cyano-4-hydroxyphenyl)butanoate To an ice cooled solution of ethyl 4-(4-hydroxyphenyl)butanoate (16.73 g, 80.32 mmol) in 200 mL of $CHCl$, was added bromine (4.15 mL, 80.8 mmol). The cooling bath was removed, and the reaction stirred at room temperature for 2 hours. The reaction mixture was then washed with water and brine, dried over sodium sulfate and concentrated to give 22.3 g (96.6%) of ethyl 4-(3-bromo-4-hydroxyphenyl)butanoate as a crystalline solid.

To a solution of ethyl 4-(3-bromo-4-hydroxyphenyl)butanoate (19.8 g, 69 mmol) in 172 mL of N-methyl-2-pyrrolidinone was added CuCN (6.49 g, 72.4 mmol). The solution was heated to reflux for 4 hours then cooled to room temperature. The reaction was diluted with EtOAc and washed twice with 5% HCl and once with brine, then dried over sodium sulfate and concentrated. Purified on silica gel using 60:40 hexanes:EtOAc as the elutant. The yield of ethyl 4-(3-cyano-4-hydroxyphenyl)butanoate was 9.84 g (61%): $^1$H-NMR ($CDCl_3$) 7.67 (1H, s), 7.24–7.29 (2H), 7.94 (1H, d), 4.14 (2H, q), 2.59 (2H, dd), 2.34 (2H, dd), 1.91 (2H, m), 1.28 (3H, t).

(b) Preparation of (R)-2-cyano-4-(3-carbethoxypropyl) phenyl Glycidyl Ether

Using the method of example 30(b), supra, ethyl 4-(3-cyano-4-hydroxyphenyl)butanoate (0.93 g, 4 mmol) and (R)-glycidyl nosylate (1.00 g, 3.86 mmol) were used to prepare 0.74 g (66%) of the title compound as a white solid.

(c) Preparation of (R)-N-[2-Hydroxy-3-(2-cyano-4-(3-carbethoxypropyl)phenoxy)propyl]-1,1-dimethyl-2-(2-naphthyl)ethylamine Hydrochloride Using the method of example 30(c), supra, (R)-2-cyano-4-(3-carbethoxypropyl)phenyl glycidyl ether (0.72 g, 2.48 mmol) and 1,1-dimethyl-2-(2-naphthyl)ethylamine (0.52 g, 2.6 mmol) were was used to prepare 0.87 g (67%) of the title compound as a white solid: $^1$H-NMR ($CDCl_3$) 9.8 (1H, br m), 8.38 (1H, br m), 7.73–7.8 (4H), 7.44 (2H, m), 7.36 (1H, d), 7.22–7.28 (3H), 6.9 (1H, d), 4.8 (1H, br m), 4.22 (2H, m), 4.12 (2H, q), 3.35–3.6 (4H), 2.53 (2H, dd), 2.26 (2H, dd), 1.85 (2H, m), 1.50 (6H, d), 1.25 (3H, t).

EXAMPLE 37

Preparation of (R)-N-[2-Hydroxy-3-(2-cyano-4-(3-carboxypropyl)phenoxy)propyl]-1,1-dimethyl-2-(2-naphthyl)ethylamine Sodium Salt (R)-N-[2-Hydroxy-3-(2-cyano-4-(3-carbethoxypropyl)phenoxy)propyl]-1,1-dimethyl-2-(2-naphthyl)ethylamine (0.618 g, 1.17 mmol) was hydrolyzed by the method of example 33, supra, to give 555 mg (90%) of the title compound as a white solid: $^1$H-NMR ($d_6$-DMSO) 7.86–7.94 (3H), 7.78 (1H, s), 7.59 (1H, d), 7.48–7.54 (3H), 7.42 (1H, d), 7.25 (1H, d), 4.22 (3H, m), 3.0–3.28 (4H, dd+br s), 2.60 (2H, dd), 2.23 (2H, dd), 1.81 (2H, m), 1.24 (6H, s).

EXAMPLE 38

Preparation of (R)-N-[2-Hydroxy-3-(2-cyano-3-(3-carbethoxypropyl)phenoxy)propyl]-1,1-dimethyl-2-(2-naphthyl)ethylamine Hydrochloride (a) Preparation of Ethyl 4-(2-cyano-3-hydroxyphenyl)butanoate Starting from 2-fluoro-6-iodobenzonitrile, the title compound was prepared as in example 32, supra, by replacing the fluoro group with a t-butoxy, replacing the iodo group with the 3-carbethoxypropyl side chain via a Suzuki coupling and ester exchange, and final removal of the t-butyl group by acid. The title compound was obtained in 49% yield over 4 steps: $^1$H-NMR (CDCl$_3$) 7.84 (1H, br s), 7.33 (1H, dd), 6.87 (1H, d), 6.82 (1H, d), 4.16 (2H, q), 2.83 (2H, dd), 2.40 (2H, dd), 2.02 (2H, m), 1.28 (3H, t); $^{13}$C NMR (CDCl$_3$) 174.28, 159.84, 146.57, 134.18, 120.98, 115.81, 114.05, 100.09, 61.09, 33.80, 33.77, 25.75, 14.29.

(b) Preparation of (R)-2-cyano-3-(3-carbethoxypropyl)phenyl Glycidyl Ether

Using the method of example 1(a), supra, ethyl 4-(2-cyano3-hydroxyphenyl)butanoate (1.9 g, 7.33 mmol) and (R)-glycidyl nosylate (1.78 g, 7.6 mmol) were used to prepare 1.70 g (80%) of the title compound as a white solid.

(c) Preparation of (R)-N-[2-Hydroxy-3-(2-cyano-3-(3-carbethoxypropyl)phenoxy)propyl]-1,1-dimethyl-2-(2-naphthyl)ethylamine Hydrochloride Using the method of example 1(b), supra, (R)-2-cyano-3-(3-carbethoxypropyl)phenyl glycidyl ether (0.8 g, 2.77 mmol) and 1,1-dimethyl-2-(2-naphthyl)ethylamine (0.58 g, 2.9 mmol) were used to prepare 1.07 g (74%) of the title compound as a white solid: $^1$H-NMR (CDCl$_3$) 9.81 (1H, br m), 8.40 (1H, br m), 7.72–7.82 (4H), 7.45 (2H, m), 7.35 (2H, m), 6.85 (1H, d), 6.81 (1H, d), 4.81 (1H, br s), 4.24 (2H, m), 4.12 (2H, q), 3.55 (2H, br m), 3.40 (2H, s), 2.77 (2H, dd), 2.33 (2H, dd), 1.95 (2H, m), 1.51 (6H, d), 1.24 (3H, t); $^{13}$C-NMR (CDCl$_3$) 173.15, 160.64, 147.29, 134.05, 133.42, 132.64, 132.16, 129.95, 128.99, 128.21, 127.95, 127.73, 126.42, 126.17, 122.26, 115.62, 110.50, 102.70, 70.94, 65.79, 61.68, 60.63, 45.31, 44.46, 33.74, 33.66, 25.77, 23.36, 23.18, 14.42.

EXAMPLE 39

Preparation of (R)-N-[2-Hydroxy-3-(2-cyano-3-(3-carboxypropyl)phenoxy)propyl]-1,1-dimethyl-2-(2-naphthyl)ethylamine Sodium Salt (R)-N-[2-Hydroxy-3-(2-cyano-3-(3-carbethoxypropyl)phenoxy)propyl]-1,1-dimethyl-2-(2-naphthyl)ethylamine (0.687 g, 1.3 mmol) was hydrolyzed by the method of example 33, supra, to give 502 mg (80%) of the title compound as a white solid:, $^1$H-NMR (D$_2$O) 7.00 (5H, m), 6.70 (3H, m), 6.53 (1H, d), 6.22 (1H, d), 3.70 (1H, br s), 3.52 (2H, br s), 2.21–2.37 (6H), 1.92 (2H, m), 1.54 (2H, m), 0.53 (5H, br s); $^{13}$C-NMR (D$_2$O) 176.89, 154.86, 142.43, 130.24, 129.08, 127.58, 126.29, 123.66, 123.13, 121.91, 121.67, 120.21, 119.65, 116.37, 110.99, 104.04, 94.82, 65.87, 63.21, 60.58, 47.80, 40.61, 38.94, 31.64, 28.23, 21.29, 20.35.

EXAMPLE 40

R)-N-[2-Hydroxy-3-(2-cyano-4-(2-carbethoxy-trans-ethylene)phenoxy)propyl]-1,1-dimethyl-2-(2-naphthyl)ethylamine (a) Ethyl-3-(2-cyano-4-hydroxyphenyl)propenoate A solution of 158.1 g (0.8 mol) of 2-cyano-4-bromophenol, 88.11 g (0.88 mol) of ethyl methacrylate, 36.5 g (0.12 mol) of tri-o-tolylphosphine and 110.6 g (0.8 mol) of potassium carbonate in 1000 mL of acetonitrile and 300 mL of water was stirred and degassed three times by alternately evacuating the flask under vacuum and then filling the flask with nitrogen. Under nitrogen 9 g (0.04 mol) of palladium (II) acetate was added and the mixture refluxed for 7 h. The reaction was diluted with 500 mL of water and the pH adjusted to 3–4 with concentrated hydrochloric acid. The mixture was then extracted with ethyl acetate. The ethyl acetate solution was dried over sodium sulfate, filtered and concentrated to approximately 500 mL. The resulting slurry was dissolved in 4 L of MeCN, heated to reflux and then poured through a 1 inch celite pad. The filtrate was concentrated to about 1.5 L and allowed to cool to room temperature over night. The solution was filtered and the solid dried under vacuum to yield 150 g of a white solid (86%).

Following the procedures described for Example 30 and 31 the title compound was obtained.

EXAMPLE 41

Inhalant Formulation

A compound of Formula (1) (1 mg to 100 mg) is aerosolized from a metered dose inhaler to deliver the desired amount of drug per use.

EXAMPLE 42

| Tablet Formulation | |
|---|---|
| Tablets/Ingredients | Per Tablet |
| 1. Active ingredient (Cmp. of Formula(I)) | 40 mg |
| 2. Corn Starch | 20 mg |
| 3. Alginic acid | 20 mg |
| 4. Sodium Alginate | 20 mg |
| 5. Mg stearate | 13 mg |

Procedure for Tablet Formulation

Ingredients 1, 2, 3 and 4 are blended in a suitable mixer/blender. Sufficient water is added portion-wise to the blend with careful mixing after each addition until the mass is of a consistency to permit its conversion to wet granules. The wet mass is converted to granules by passing it through an oscillating granulator using a No. 8 mesh (2.38 mm) screen. The wet granules are then dried in an oven at 140° F. (60° C.) until dry. The dry granules are lubricated with ingredient No. 5, and the lubricated granules are compressed on a suitable tablet press.

EXAMPLE 43

Parenteral Formulation

A pharmaceutical composition for parenteral administration is prepared by dissolving an appropriate amount of a compound of Formula (I) in polyethylene glycol with heating. This solution is then diluted with water for injections (to 100 ml). The solution is then rendered sterile by filtration through a 0.22 micron membrane filter and sealed in sterile containers.

All publications, including but not limited to patents and patent applications cited in this specification are herein incorporated by reference as if each individual publication were specifically and individually indicated to be incorporated by reference as though fully set forth.

What is claimed is:

1. A compound according to Formula (I) hereinbelow:

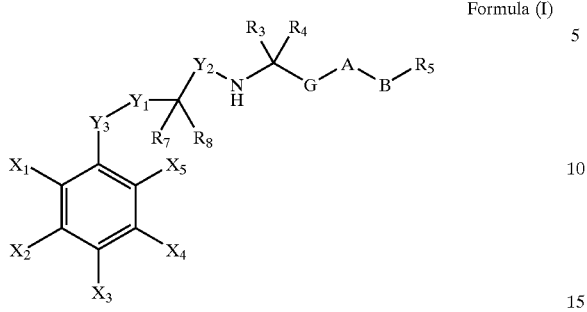

Formula (I)

wherein:

$Y_1$ is a covalent bond, alkylene or alkenylene of up to 4 carbon atoms, unsubstituted or substituted by $C_{1-4}$ alkyl, or O;

$Y_2$ is methylene, unsubstituted or substituted by $C_{1-4}$ alkyl or haloalkyl;

$Y_3$ is covalent bond or O;

$R_3$ and $R_4$ are, independently, methyl or ethyl, or, together, form cyclopropyl;

$R_5$ is aryl or fused aryl, dihydro or tetrahydro fused aryl, unsubstituted or substituted with any substituents being selected from the group consisting of OH, halogen, $C_{1-4}$ alkyl, $C_{1-4}$ alkoxy, $C_{3-6}$ cycloalkyl, $OSO_2R^{IV}$, $NO_2$, $OCF_3$, $CF_3$, $CH_2CF_3$, $(CH_2)_nCO_2R^{IV}$, and $O-(CH_2)_nCO_2R^{IV}$, wherein n is an integer from 0 to 3 and $R^{IV}$ is selected from the group consisting of H, $C_{1-4}$ alkyl, and $C_{3-6}$ cycloalkyl;

G is a covalent bond, $CHR_6$, CH, COH, or C=O;

$R_7$ is H, OH, or O—$C_{1-4}$ alkyl;

$R_8$ is H or $C_{14}$ alkyl; or $R_7$ and $R_8$ together form a ketone;

A and B are, independently, selected from the group consisting of a bond, $CH_2$, NH, O, S and C=O, provided that either A or B is selected from $CH_2$ and NH; or A and B together form a bond; or the A-B moiety is represented by CH=CH or C≡C;

wherein $X_1$ and $X_5$ are independently selected from the group consisting of H, halogen, $NO_2$, $C_{1-4}$ alkyl, cycloalkcyl, $CH_2$-aryl, and $CH_2$-heteroaryl; provided that either $X_1$ or $X_5$ is H;

$X_2$, $X_3$ and $X_4$ are selected from the group consisting of H, halogen, O—$C_{1-4}$ alkyl, O-aryl, $CH_2$-aryl, alkyl, C(O)aryl, CH(OH)aryl, and J—K;

J is a covalent bond alkylene, O-alkylene or alkenylene of up to 5 carbon atoms, unsubstituted or substituted by a substituent selected from the group consisting of $C_{1-4}$ alkyl, OH, O(forming a ketone), aryl, heteroaryl, and NR'R", wherein R' and R" are independently selected from the group consisting H, alkyl, aryl, heteroaryl, C(O)alkyl, C(O)aryl, and C(O)heteroaryl;

K is selected from the group consisting of, $CO_2R^{IV}$, OH, and CN;

and a pharmaceutically acceptable salt or complex thereof.

2. A compound according to claim 1 having the structure according to Formula (II) hereinbelow:

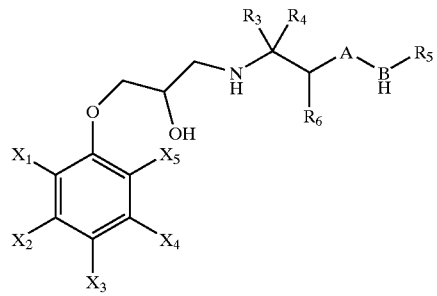

Formula (II)

wherein:

$R_3$ and $R_4$ are, independently, methyl or ethyl, or, together, form cyclopropyl;

$R_5$ is aryl or fused aryl, or dihydro or tetrahydro fused aryl, unsubstituted or substituted with any substituents being selected from the group consisting of OH, halogen, $C_{1-4}$ alkyl, $C_{1-4}$ alkoxy, $C_{3-6}$ cycloalkyl, $OSO_2R^{IV}$, CN, $NO_2$, $OCF_3$, $CF_3$, $CH_2CF_3$, wherein $R^{IV}$ is selected from the group consisting of H, $C_{1-4}$ alkyl, $C_{3-6}$ cycloalkyl, $C_{3-6}$ cycloalkyl;

$R_6$ is H, OH or O (forming a ketone); and

A and B are, independently, selected consisting of a bond, $CH_2$, NH, O, S and C=O, provided that either A or B is selected from $CH_2$ and NH; or A and B together form a bond; or the A-B moiety is represented by CH=CH or C≡C.

$X_1$ and $X_5$ are independently selected from the group consisting of H, halogen, $NO_2$, $C_{1-4}$ alkyl, cycloalkyl, $CH_2$-aryl, and $CH_2$-heteroaryl; provided that either $X_1$ or $X_5$ is H;

$X_2$, $X_3$ and $X_4$ are selected from the group consisting of H, halogen, O—$C_{1-4}$ akyl, O-aryl, $CH_2$-aryl, alkyl, C(O)aryl, CH(OH)aryl and J—K J is a covalent bond, alkylene, O-alkenylene or alkenylene of up to 5 carbon atoms, unsubstituted or substituted by a substituent selected from the group consisting of $C_{1-4}$ alkyl, OH, O(ketone), aryl, heteroaryl, and NR'R", wherein R' and R" are independently selected from the group consisting of H, alkyl, aryl, heteroaryl, C(O)alkyl, C(O)aryl, and C(O)heteroaryl;

K is selected from the group consisting of $CO_2H$, $CO_2R^{IV}$, OH, and CN.

3. A compound according to claim 2 wherein:

$R_5$ is aryl or fused aryl or dihyro or tetrahydro aryl, unsubstituted or substituted with any substituents being selected from the group consisting of $OCH_3$, $CH_2CH_3$, halogen, $C_{3-6}$ heterocycloalkyl, CN, $NO_2$, $OCF_3$, $CF_3$, $CH_2CF_3$;

$R_6$ is H;

A and B are, independently, selected from the group consisting of a bond, $CH_2$, NH, O, S and C=O, provided that either A or B selected from $CH_2$ and NH, or A and B together form a bond;

$X_1$ and $X_5$ are selected from the group consisting of Cl, F, and $NO_2$;

provided that either $X_1$ or $X_5$ is H;

$X_2$, $X_3$ and $X_4$ are independently selected from the group consisting of H, F, Cl, CN, O-aryl, $CH_2$-aryl, C(O)aryl, CH(OH)aryl, and J—K;

J is a covalent bond, alkylene, alkenylene or O alkylene of up to 5 carbon atoms, unsubstituted or substituted by $C_{1-4}$ alkyl, aryl, heteroaryl, or NR'R", wherein R' and R" are independently selected from the group consisting H, alkyl, aryl, heteroaryl, C(O)alkyl, C(O)aryl, and C(O)heteroaryl; and K is $CO_2R^{IV}$.

4. A compound according to claim 3 wherein:

$R_5$ is phenyl, or naphthyl, $R_6$ is H;

A and B are, independently, selected from the group consisting of a bond, $CH_2$, and O, or A and B together form a bond;

$X_1$ and $X_5$ are independently Cl, or $NO_2$; provided that either $X_1$ or $X_5$ is H;

$X_2$ or $X_3$ or $X_4$ are H, CN, Cl or J—K;

J is a covalent bond, alkylene or alkenylene of up to 5 carbon atoms, unsubstituted or substituted by aryl, heteroaryl, or NR'R", wherein R' and R" are selected from the group consisting of H, alkyl, aryl, heteroaryl, C(O)alkyl, C(O)aryl, and C(O)heteroaryl; and K is $CO_2R^{IV}$.

5. A compound according to claim 1 selected from the group consisting of:

(R)-N-[2-Hydroxy-3-(2-cyano-4-(2-carboethoxyethyl)phenoxy)propyl]-1,1-dimethyl-2-(2-naphthyl)ethylamine;

(R)-N-[2-Hydroxy-3-(2-cyano-4-(2-carboxyethyl)phenoxy)propyl]-1,1-dimethyl-2-(2-naphthyl)ethylamine;

(R)-N-[2-Hydroxy-3-(2-cyano-5-(3-carbethoxypropyl)phenoxy)propyl]-1,1-dimethyl-2-(2-naphthyl)ethylamine;

(R)-N-[2-Hydroxy-3-(2-cyano-5-(3-carboxypropyl)phenoxy)propyl]-1,1-dimethyl-2-(2-naphthyl)ethylamine;

(R)-N-[2-Hydroxy-3-(2-cyano-5-(2-carbethoxyethyl)phenoxy)propyl]-1,1-dimethyl-2-(2-naphthyl)ethylamine;

(R)-N-[2-Hydroxy-3-(2-cyano-5-(2-carboxyethyl)phenoxy)propyl]-1,1-dimethyl-2-(2-naphthyl)ethylamine;

(R)-N-[2-Hydroxy-3-(2-cyano-4-(3-carbethoxypropyl)phenoxy)propyl]-1,1-dimethyl-2-(2-naphthyl)ethylamine;

(R)-N-[2-Hydroxy-3-(2-cyano-4-(3-carboxypropyl)phenoxy)propyl]-1,1-dimethyl-2-(2-naphthyl)ethylamine;

(R)-N-[2-Hydroxy-3-(2-cyano-3-(3-carbethoxypropyl)phenoxy)propyl]-1,1-dimethyl-2-(2-naphthyl)ethylamine;

(R)-N-[2-Hydroxy-3-(2-cyano-3-(3-carboxypropyl)phenoxy)propyl]-1,1-dimethyl-2-(2-naphthyl)ethylamine;

(R)-N-[2-Hydroxy-3-(2-cyano-3-(2-carbethoxyethyl)phenoxy)propyl]-1,1-dimethyl-2-(2-naphthyl)ethylamine;

(R)-N-[2-Hydroxy-3-(2-cyano-3-(2-carboxyethyl)phenoxy)propyl]-1,1-dimethyl-2-(2-naphthyl)ethylamine;

(R)-N-[2-Hydroxy-3-(2-cyano-4-(carbethoxymethyl)phenoxy)propyl]-1,1-dimethyl-2-(2-naphthyl)ethylamine;

(R)-N-[2-Hydroxy-3-(2-cyano-4-(carboxymethyl)phenoxy)propyl]-1,1-dimethyl-2-(2-naphthyl)ethylamine;

(R)-N-[2-Hydroxy-3-(2-cyano-5-(carbethoxymethyl)phenoxy)propyl]-1,1-dimethyl-2-(2-naphthyl)ethylamine;

(R)-N-[2-Hydroxy-3-(2-cyano-5-(carboxymethyl)phenoxy)propyl]-1,1-dimethyl-2-(2-naphthyl)ethylamine;

(R)-N-[2-Hydroxy-3-(2-cyano-4-(2-carbethoxy-trans-ethylene)phenoxy)propyl]-1,1-dimethyl-2-(2-naphthyl)ethylamine;

(R)-N-[2-Hydroxy-3-(2-cyano-4-(2-carboxy-trans-ethylene)phenoxy)propyl]-1,1-dimethyl-2-(2-naphthyl)ethylamine;

(R)-1-[1,1-dimethyl-2-(4-methoxyphenyl)ethylamino]-3-(4-(2-phenyl-2-R,S-methoxycarbonylethyl))phenoxy]-propan-2-ol;

(R)-1-[1,1-dimethyl-2-(4-methoxyphenyl)ethylamino]-3-[(4-(2-phenyl-2-R,S-carboxyethyl)phenoxy]-propan-2-ol;

(R)-1-[1,1-dimethyl-2-(4-methoxyphenyl)ethylamino]-3-[(3-(3-benzyl-4-methoxycarbonylmethyl)phenoxy]-propan-2-ol;

(R)-1-[1,1-dimethyl-2-(2-naphthyl)ethylamino]-3-[(3-benzyl-4-methoxycarbonylmethyl)phenoxy]-propan-2-ol;

(R)-1-[1,1-dimethyl-2-(2-naphthyl)ethylamino]-3-[(3-benzyl-4-carboxymethyl)phenoxy]-propan-2-ol;

(R)-1-[1,1-dimethyl-2-(4-methoxyphenyl)ethylamino]-3-[(3-benzyl-4-carboxymethyl)phenoxy]-propan-2-ol;

(R)-1-[1,1-dimethyl-2-(4-methoxyphenyl)ethylamino]-3-[(4-(3-hydroxy)propyl)phenoxy]-propan-2-ol;

(R)-1-[1,1-dimethyl-2-(4-methoxyphenyl)ethylamino]-3-[(4-(2-hydroxy)ethyl)phenoxy]-propan-2-ol;

(R)-1-[1,1-dimethyl-2-(4-methoxyphenyl)ethylamino]-3-[(4-(2-cyano)ethyl)phenoxy]-propan-2-ol; (R)-1-[1,1-dimethyl-2-(4-methoxyphenyl)ethylamino]-3-[(4-cyanomethyl)phenoxy]-propan-2-ol;

(R)-1-[1,1-dimethyl-2-(4-methoxyphenyl)ethylamino]-3-[(4-cyano)phenoxy]-propan-2-ol;

(R)-1-[1,1-dimethyl-2-(4-methoxyphenyl)ethylamino]-3-[(4-methoxycarbonylmethyl)phenoxy]-propan-2-ol;

(R)-1-[1,1-dimethyl-2-(4-methoxyphenyl)ethylamino]-3-[(2-nitro-4-cyano)phenoxy]-propan-2-ol;

(R)-1-[1,1-dimethyl-2-(4-methoxyphenyl)ethylamino]-3-[(2-nitro-4-(hydroxymethyl)phenoxy]-propan-2-ol;

(R)-1-[1,1-dimethyl-2-(4-methoxyphenyl)ethylamino]-3-[(2-nitro-4-methoxycarbonylmethyl)phenoxy]-propan-2-ol;

(R)-1-[1,1-dimethyl-2-(4-methoxyphenyl)ethylamino]-3-[(2-nitro-4-carboxymethyl)phenoxy]-propan-2-ol;

(R)-1-[1,1-dimethyl-2-(2-naphthyl)ethylamino]-3-[(4-methoxycarbonyl)phenoxy]-propan-2-ol;

(R)-1-[1,1-dimethyl-2-(2-naphthyl)ethylamino]-3-[(4-carboxy)phenoxy]-propan-2-ol;

(R)-1-[1,1-dimethyl-2-(4-methoxyphenyl)ethylamino]-3-[(2-cyano-4-ethoxycarbonylmethyl)phenoxy]-propan-2-ol;

(R)-1-[1,1-dimethyl-2-(4-methoxyphenyl)ethylamino]-3-[(2-cyano-4-carboxymethyl)phenoxy]-propan-2-ol;

(R)-1-[1,1-dimethyl-2-(4-methoxyphenyl)ethylamino]-3-[(4-methoxycarbonylethyl)phenoxy]-propan-2-ol;

N-[2R-hydroxy-3-[[2-nitro-4-[2S-ethoxycarbonyl-2-[methylsulfonyl]amino]phenoxy]propyl]-1,1-dimethyl-2-[4-methoxyphenyl]ethylamine;

N-[2R-hydroxy-3-[[2-nitro-4-[2S-carboxy-2-[[[2-carboxy]phenyl]carbonyl]amino]ethyl]phenoxy]propyl]-1,1-dimethyl-2-[naphthyl]ethylamine;

N-[2R-hydroxy-3-[[2-nitro-4-[2S-methoxycarbonyl-2-[[[2-carboxy]phenyl]carbonyl]amino]ethyl]phenoxy]propyl]-1,1-dimethyl-2-[naphthyl]ethylamine;

(R)-1-[1,1-dimethyl-2-(2-naphthyl)ethylamino]-3-[(3-(2-aminophenoxy)-4-methoxycarbonyl)phenoxy]-propan-2-ol; and (R)-1-[1,1-dimethyl-2-(2-naphthyl)ethylamino]-3-[(3-(2-aminophenoxy)-4-carboxy)phenoxy]-propan-2-ol;

and a pharmaceutically acceptable salt or complex thereof.

6. A compound according to claim 5 selected from the group consisting of:

(R)-N-[2-Hydroxy-3-(2-cyano-4-(2-carboethoxyethyl)phenoxy)propyl]-1,1-dimethyl-2-(2-naphthyl)ethylamine;

(R)-N-[2-Hydroxy-3-(2-cyano-4-(2-carboxyethyl)phenoxy)propyl]-1,1-dimethyl-2-(2-naphthyl)ethylamine;

(R)-N-[2-Hydroxy-3-(2-cyano-5-(3-carbethoxypropyl)phenoxy)propyl]-1,1-dimethyl-2-(2-naphthyl)ethylamine;

(R)-N-[2-Hydroxy-3-(2-cyano-5-(3-carboxypropyl)phenoxy)propyl]-1,1-dimethyl-2-(2-naphthyl)ethylamine;

(R)-N-[2-Hydroxy-3-(2-cyano-5-(2-carbethoxyethyl)phenoxy)propyl]-1,1-dimethyl-2-(2-naphthyl)ethylamine;

(R)-N-[2-Hydroxy-3-(2-cyano-5-(2-carboxyethyl)phenoxy)propyl]-1,1-dimethyl-2-(2-naphthyl)ethylamine;

(R)-N-[2-Hydroxy-3-(2-cyano-4-(3-carbethoxypropyl)phenoxy)propyl]-1,1-dimethyl-2-(2-naphthyl)ethylamine;

(R)-N-[2-Hydroxy-3-(2-cyano-4-(3-carboxypropyl)phenoxy)propyl]-1,1-dimethyl-2-(2-naphthyl)ethylamine;

(R)-N-[2-Hydroxy-3-(2-cyano-3-(3-carbethoxypropyl)phenoxy)propyl]-1,1-dimethyl-2-(2-naphthyl)ethylamine;

(R)-N-[2-Hydroxy-3-(2-cyano-3-(3-carboxypropyl)phenoxy)propyl]-1,1-dimethyl-2-(2-naphthyl)ethylamine;

(R)-N-[2-Hydroxy-3-(2-cyano-3-(2-carbethoxyethyl)phenoxy)propyl]-1,1-dimethyl-2-(2-naphthyl)ethylamine;

(R)-N-[2-Hydroxy-3-(2-cyano-3-(3-carboxyethyl)phenoxy)propyl]-1,1-dimethyl-2-(2-naphthyl)ethylamine;

(R)-N-[2-Hydroxy-3-(2-cyano-4-(carbethoxymethyl)phenoxy)propyl]-1,1-dimethyl-2-(2-naphthyl)ethylamine;

(R)-N-[2-Hydroxy-3-(2-cyano-4-(carboxymethyl)phenoxy)propyl]-1,1-dimethyl-2-(2-naphthyl)ethylamine;

(R)-N-[2-Hydroxy-3-(2-cyano-5-(carbethoxymethyl)phenoxy)propyl]-1,1-dimethyl-2-(2-naphthyl)ethylamine;

(R)-N-[2-Hydroxy-3-(2-cyano-5-(carboxymethyl)phenoxy)propyl]-1,1-dimethyl-2-(2-naphthyl)ethylamine;

(R)-N-[2-Hydroxy-3-(2-cyano-4-(2-carbethoxy-trans-ethylene)phenoxy)propyl]-1,1-dimethyl-2-(2-naphthyl)ethylamine;

(R)-N-[2-Hydroxy-3-(2-cyano-4-(2-carboxy-trans-ethylene)phenoxy)propyl]-1,1-dimethyl-2-(2-naphthyl)ethylamine;

(R)-1-[1,1-dimethyl-2-(2-naphthyl)ethylamino]-3-[(3-(2-aminophenoxy)-4-methoxycarbonyl)phenoxy]-propan-2-ol;

(R)-1-[1,1-dimethyl-2-(4-methoxyphenyl)ethylamino]-3 (4-(2-phenyl-2-R,S-methoxycarbonylethyl)phenoxy]-propan-2-ol;

(R)-1-[1,1-dimethyl-2-(4-methoxyphenyl)ethylamino]-3-[(3-benzyl-4-methoxycarbonylmethyl)phenoxy]-propan-2-ol;

(R)-1-[1,1-dimethyl-2-(2-naphthyl)ethylamino]-3-[(3-benzyl-4-methoxycarbonylmethyl)phenoxy]-propan-2-ol;

(R)-1-[1,1-dimethyl-2-(2-naphthyl)ethylamino]-3-[(3-benzyl-4-carboxymethyl)phenoxy]-propan-2-ol;

(R)-1-[1,1-dimethyl-2-(4-methoxyphenyl)ethylamino]-3-[(2-cyano-4-ethoxycarbonylmethyl)phenoxy]-propan-2-ol;

(R)-1-[1,1-dimethyl-2-(4-methoxyphenyl)ethylamino]-3-[(2-nitro-4-methoxycarbonylmethyl)phenoxy]-propan-2-ol;

(R)-1-[1,1-dimethyl-2-(2-naphthyl)ethylamino]-3-[(4-methoxycarbonyl)phenoxy]-propan-2-ol; N-[2R-hydroxy-3-[[2-nitro-4-[2S-ethoxycarbonyl-2-[methylsulfonyl]amino]phenoxy]propyl]-1,1-dimethyl-2-[4-methoxyphenyl]ethylamine;

N-[2R-hydroxy-3-[[2-nitro-4-[2S-methoxycarbonyl-2-[[[2-carboxy]phenyl]carbonyl]amino]ethyl]phenoxy]propyl]-1,1-dimethyl-2-[naphthyl]ethylamine; and a pharmaceutically acceptable salt or complex thereof.

7. A compound according to claim 6 selected from the group consisting of:

(R)-N-[2-Hydroxy-3-(2-cyano-4-(2-carboethoxyethyl)phenoxy)propyl]-1,1-dimethyl-2-(2-naphthyl)ethylamine;

(R)-N-[2-Hydroxy-3-(2-cyano-4-(2-carboxyethyl)phenoxy)propyl]-1,1-dimethyl-2-(2-naphthyl)ethylamine;

(R)-N-[2-Hydroxy-3-(2-cyano-5-(3-carbethoxypropyl)phenoxy)propyl]-1,1-dimethyl-2-(2-naphthyl)ethylamine;

(R)-N-[2-Hydroxy-3-(2-cyano-5-(3-carboxypropyl)phenoxy)propyl]-1,1-dimethyl-2-(2-naphthyl)ethylamine;

(R)-N-[2-Hydroxy-3-(2-cyano-5-(2-carbethoxyethyl)phenoxy)propyl]-1,1-dimethyl-2-(2-naphthyl)ethylamine;

(R)-N-[2-Hydroxy-3-(2-cyano-5-(2-carboxyethyl)phenoxy)propyl]-1,1-dimethyl-2-(2-naphthyl)ethylamine;

(R)-N-[2-Hydroxy-3-(2-cyano-4-(3-carbethoxypropyl)phenoxy)propyl]-1,1-dimethyl-2-(2-naphthyl)ethylamine;

(R)-N-[2-Hydroxy-3-(2-cyano-4-(3-carboxypropyl)phenoxy)propyl]-1,1-dimethyl-2-(2-naphthyl)ethylamine;

(R)-N-[2-Hydroxy-3-(2-cyano-3-(3-carbethoxypropyl)phenoxy)propyl]-1,1-dimethyl-2-(2-naphthyl)ethylamine;

(R)-N-[2-Hydroxy-3-(2-cyano-3-(3-carboxypropyl)phenoxy)propyl]-1,1-dimethyl-2-(2-naphthyl)ethylamine;

(R)-N-[2-Hydroxy-3-(2-cyano-3-(2-carbethoxyethyl)phenoxy)propyl]-1,1-dimethyl-2-(2-naphthyl)ethylamine;

(R)-N-[2-Hydroxy-3-(2-cyano-3-(3-carboxyethyl)phenoxy)propyl]-1,1-dimethyl-2-(2-naphthyl)ethylamine;

(R)-N-[2-Hydroxy-3-(2-cyano-4-(carbethoxymethyl)phenoxy)propyl]-1,1-dimethyl-2-(2-naphthyl)ethylamine;

(R)-N-[2-Hydroxy-3-(2-cyano-4-(carboxymethyl)phenoxy)propyl]-1,1-dimethyl-2-(2-naphthyl)ethylamine;

(R)-N-[2-Hydroxy-3-(2-cyano-5-(carbethoxymethyl)phenoxy)propyl]-1,1-dimethyl-2-(2-naphthyl)ethylamine;

(R)-N-[2-Hydroxy-3-(2-cyano-5-(carboxymethyl)phenoxy)propyl]-1,1-dimethyl-2-(2-naphthyl)ethylamine;

(R)-N-[2-Hydroxy-3-(2-cyano-4-(2-carbethoxy-trans-ethylene)phenoxy)propyl]-1,1-dimethyl-2-(2-naphthyl)ethylamine;

(R)-N-[2-Hydroxy-3-(2-cyano-4-(2-carboxy-trans-ethylene)phenoxy)propyl]-1,1-dimethyl-2-(2-naphthyl)ethylamine; and (R)-1-[1,1-dimethyl-2-(2-naphthyl)ethylamino]-3-[(3-(2-aminophenoxy)-4-methoxycarbonyl)phenoxy]-propan-2-ol; and and a pharmaceutically acceptable salt or complex thereof.

8. A pharmaceutical composition for use in treating a disease or disorder involving an abnormal bone or mineral homeostasis which comprises a compound according to claim 1 and a pharmaceutically acceptable carrier.

9. A method of antagonizing a calcium receptor which comprises administering to a subject in need thereof an effective amount of a compound according to claim 1.

10. A method of treating a disease or disorder involving an abnormal bone or mineral homeostasis which comprises administering to a subject in need of treatment thereof an effective amount of a compound according to claim 1.

11. A method according to claim 9 wherein the bone or mineral disease or disorder is selected from the group consisting of osteosarcoma, periodontal disease, fracture healing, osteoarthritis, rheumatoid arthritis, Paget's disease, humoral hypercalcemia, malignancy and osteoporosis.

12. A method according to claim 10 wherein the bone or mineral disease or disorder is osteoporosis.

13. A method of increasing serum parathyroid levels which comprises administering to a subject in need of treatment an effective amount of a compound according to claim 1.

* * * * *